United States Patent
Homan et al.

(10) Patent No.: US 8,016,756 B2
(45) Date of Patent: Sep. 13, 2011

(54) MEDICAL SYSTEM AND METHOD OF SWITCHING ANTENNA

(75) Inventors: Masatoshi Homan, Hino (JP); Tomoya Takenaka, Oita (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/769,089

(22) Filed: Apr. 28, 2010

(65) Prior Publication Data

US 2010/0280340 A1   Nov. 4, 2010

Related U.S. Application Data

(63) Continuation of application No. PCT/JP2009/067711, filed on Oct. 13, 2009.

(30) Foreign Application Priority Data

Oct. 14, 2008  (JP) .................................. 2008-265698
Oct. 14, 2008  (JP) .................................. 2008-265700

(51) Int. Cl.
  *A61B 5/07*  (2006.01)
  *A61B 5/00*  (2006.01)
(52) U.S. Cl. ........................................ 600/302; 600/300
(58) Field of Classification Search .......... 600/300–302, 600/481
  See application file for complete search history.

(56) References Cited

U.S. PATENT DOCUMENTS

| | | | |
|---|---|---|---|
| 5,862,803 A * | 1/1999 | Besson et al. | 600/508 |
| 5,957,854 A * | 9/1999 | Besson et al. | 600/509 |
| 6,289,238 B1 * | 9/2001 | Besson et al. | 600/509 |
| 6,577,893 B1 * | 6/2003 | Besson et al. | 600/509 |
| 7,215,991 B2 * | 5/2007 | Besson et al. | 600/509 |
| 2004/0015058 A1 * | 1/2004 | Besson et al. | 600/301 |
| 2005/0043634 A1 | 2/2005 | Yokoi et al. | |
| 2007/0208235 A1 * | 9/2007 | Besson et al. | 600/301 |
| 2007/0265496 A1 | 11/2007 | Kawano et al. | |
| 2008/0033257 A1 | 2/2008 | Yokoi et al. | |
| 2008/0297291 A1 | 12/2008 | Kawano et al. | |
| 2008/0300453 A1 | 12/2008 | Aoki et al. | |
| 2008/0318540 A1 | 12/2008 | Homan et al. | |
| 2009/0171146 A1 | 7/2009 | Fujita | |

(Continued)

FOREIGN PATENT DOCUMENTS

JP   2005-13338   1/2005

(Continued)

OTHER PUBLICATIONS

International Search Report dated Jan. 19, 2010.

*Primary Examiner* — Charles A Marmor, II
*Assistant Examiner* — Navin Natnithithadha
(74) *Attorney, Agent, or Firm* — Scully, Scott, Murphy & Presser, P.C.

(57) ABSTRACT

A medical system includes a capsule type medical apparatus introduced into a subject and having an antenna having directionality and a communication unit which executes a communication through the antenna, an external antenna, which is disposed outside of the subject and has an antenna having directionality and an antenna disposed together with the antenna and having directionality in a direction different from the antenna, and an external machine having a selection unit which selects any of the antennas in the external antenna and a second communication unit which executes a communication with the first communication unit through the antenna whose polarized wave surface is selected by the selection unit.

17 Claims, 29 Drawing Sheets

U.S. PATENT DOCUMENTS

| | | | |
|---|---|---|---|
| 2009/0189609 A1* | 7/2009 | Eberler et al. | 324/322 |
| 2009/0196476 A1 | 8/2009 | Inoue | |

FOREIGN PATENT DOCUMENTS

| | | |
|---|---|---|
| JP | 2006-340888 | 12/2006 |
| JP | 2007-111265 | 5/2007 |
| JP | 2007-175448 | 7/2007 |
| JP | 2007-195961 | 8/2007 |
| JP | 2008-36243 | 2/2008 |
| WO | WO 2008/032713 A1 | 3/2008 |

* cited by examiner

RECEIVING STRENGTH POSITION DEPENDENCE
TO VERTICAL POLARIZED WAVE

RECEIVING STRENGTH POSITION DEPENDENCE
TO HORIZONTAL POLARIZED WAVE

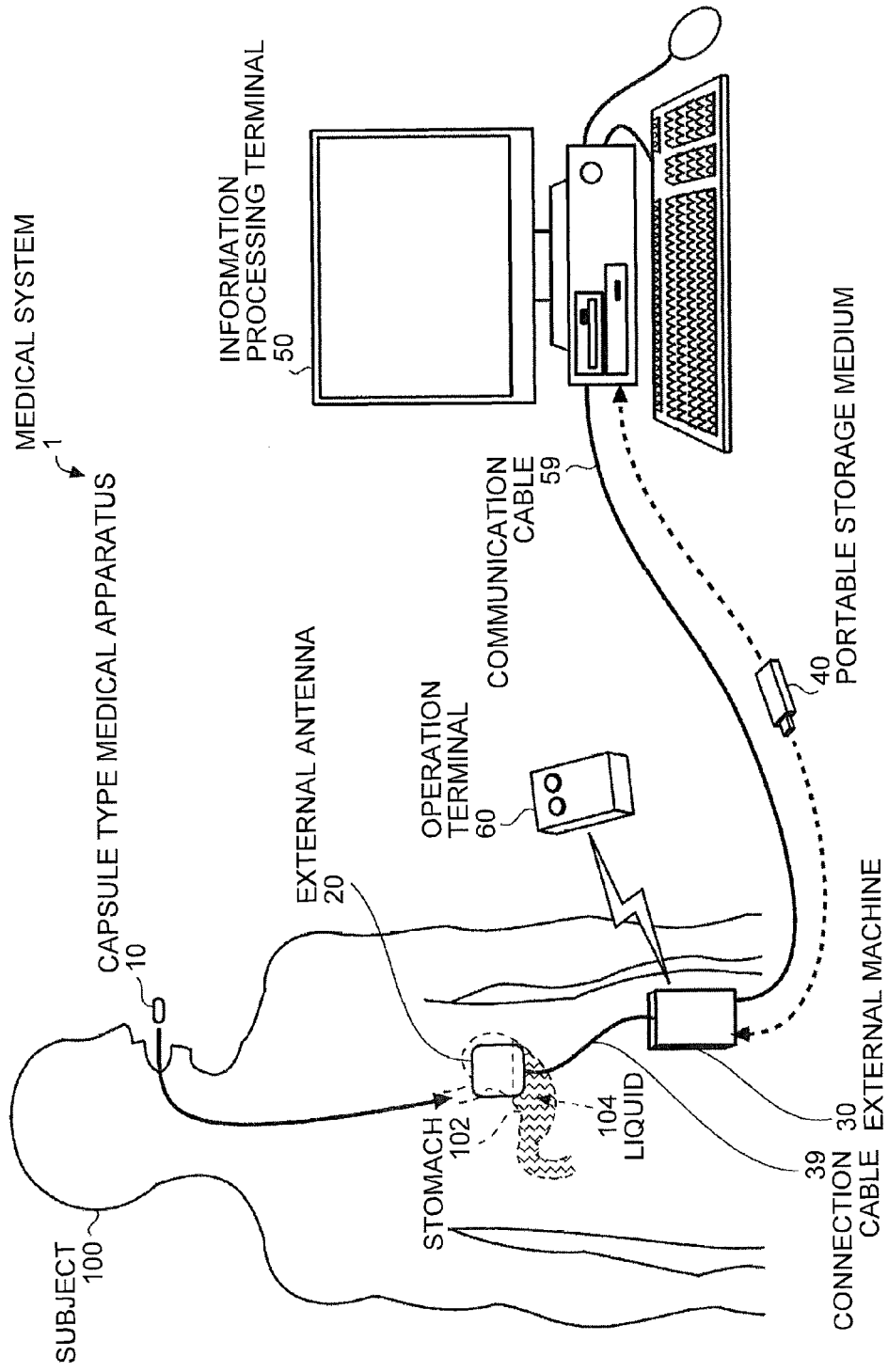

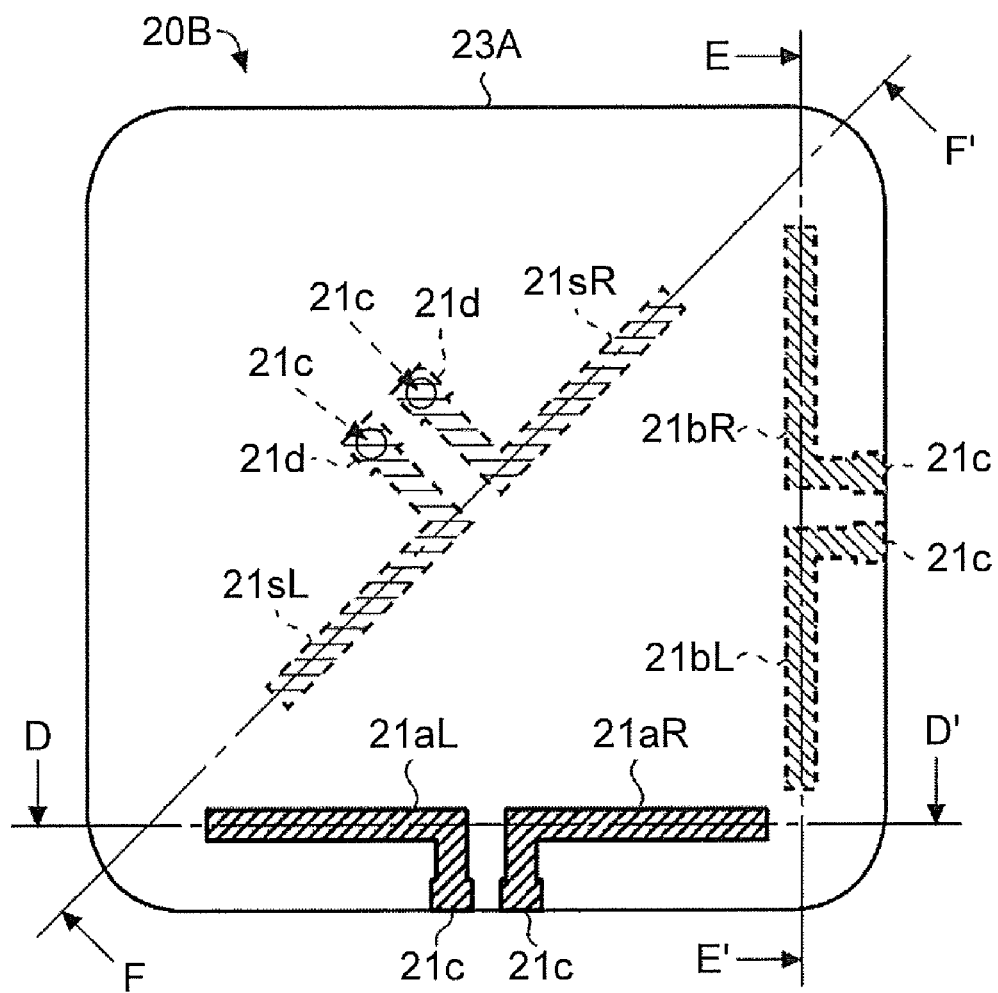

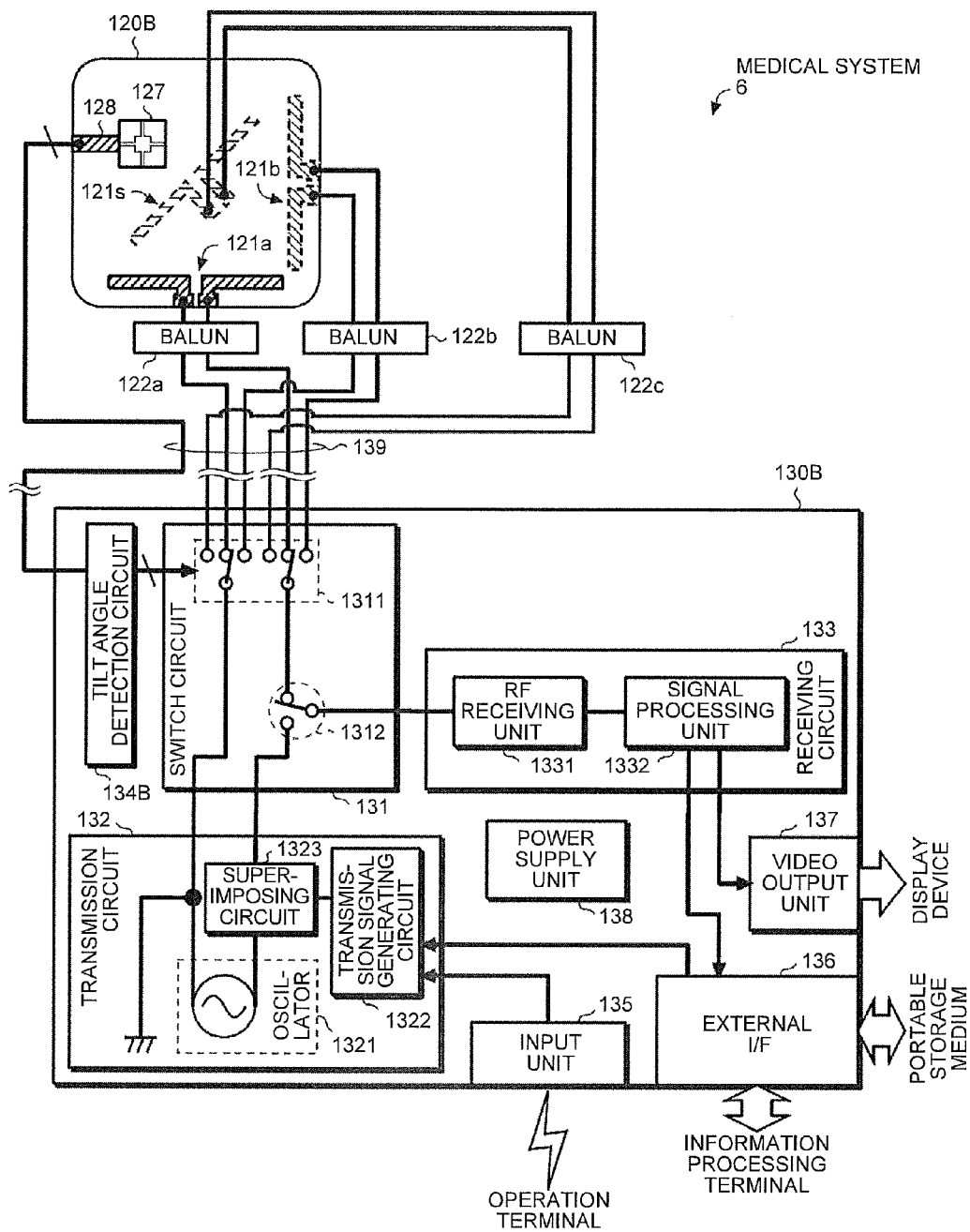

MEDICAL SYSTEM AND METHOD OF SWITCHING ANTENNA

CROSS-REFERENCE TO RELATED APPLICATIONS

This application is a continuation of PCT international application Ser. No. PCT/JP2009/067711 filed on Oct. 13, 2009 which designates the United States, incorporated herein by reference.

BACKGROUND OF INVENTION

1. Field of the Invention

The present invention relates to a medical system and an antenna switching method, and more particularly to a medical system and an antenna switching method in and by which a capsule type medical apparatus introduced into a subject such as a person, an animal, and the like executes a wireless communication with an external machine disposed outside of the subject.

2. Description of the Related Art

In, for example, a medical field, a swallow-type capsule type medical apparatus has conventionally existed which has an information acquisition function for obtaining various kinds of information in a subject by being introduced into the subject such as a person, an animal, and the like and a wireless communication function for transmitting and receiving the obtained information, a control signal from an outside, and the like through a wireless line (refer to, for example, Japanese Application Patent Publication No. 2007-195961, Japanese Application Patent Publication No. 2007-175448, Japanese Application Patent Publication No. 2005-13338).

In a medical system using the capsule type medical apparatus as described above, a coil antenna (also called a loop antenna) is often used as a transmission/receiving antenna contained in the capsule type medical apparatus (refer to, for example, a paragraph 0039 of Japanese Application Patent Publication No. 2007-195961). This is because the coil antenna has a large gain in small antennas.

In contrast, the transmission/receiving antenna on an external machine side is ordinarily disposed in intimate contact with or close to the subject to improve a reception sensitivity of a radio wave radiated from the capsule type medical apparatus in the subject. Further, to permit a movement of the subject in a state that an antenna of the external machine is attached to the subject, the antenna of the external machine is ordinarily portably attached to the subject (refer to, for example, a paragraph 0027 or FIG. 1 of Japanese Application Patent Publication No. 2007-195961, for example, a paragraph 0021 or FIG. 1 of Japanese Application Patent Publication No. 2007-175448, or a paragraph 0035 or FIGS. 1 and 4 of Japanese Application Patent Publication No. 2005-13338). Thus, in general, an antenna having a simple configuration such as a dipole antenna, a loop antenna, and the like has been conventionally used as the antenna on the external machine side in consideration of portability and the like for the subject.

However, ordinarily, the coil antenna used as an antenna for the capsule type medical apparatus has directionality. Further, the dipole antenna or the loop antenna used as an antenna for the external machine also has directionality.

Here, FIGS. 1A and 1C show a relation between a mutual position and a reception strength (reception strength position dependence) obtained by an experiment for receiving a radio wave radiated from a coil antenna by a dipole antenna. FIG. 1A shows the reception strength position dependence to a vertical polarized wave when a coil antenna is disposed so that a winding axis is horizontal to the ground surface, and FIG. 1C shows the reception strength position dependence to a horizontal polarized wave when the coil antenna is disposed so that the winding axis is vertical to the ground surface likewise. Further, FIG. 1B shows a conceptual view showing a positional relation between a transmission antenna (coil antenna) and a reception antenna (dipole antenna) to explain the reception strength position dependence of FIG. 1A, and FIG. 1D shows a conceptual view showing the positional relation between the transmission antenna (coil antenna) and the reception antenna (dipole antenna) to explain the reception strength position dependence of FIG. 10. Note that, as shown in FIGS. 1B and 1D, respectively, the reception strength position dependency properties shown in FIG. 1A and FIG. 10 were obtained from a result of measurement of a strength of a radio wave received by a dipole antenna 1003 using a spectrum analyzer in a state that a coil antenna 1002 having a diameter of 3 mm was introduced into a cylindrical liquid phantom (simulated human body) 1001 having a diameter of 300 mm and a height of 300 mm and further the dipole antenna 1003 was caused to come into intimate contact with a side surface of the liquid phantom 1001. Note that a distance between the transmission antenna (coil antenna 1002) and the reception antenna (dipole antenna 1003) at the time was assumed to be 150 mm. Here, the vertical polarized wave is a radio wave, in which an electric field travels on a surface vertical to the ground surface and is a polarized wave which travels on a surface vertical to a winding axis of the coil antenna 1002 in FIG. 1B. Further, the horizontal polarized wave is a radio wave, in which an electric field travels on a surface horizontal to the ground surface, and is a polarized wave which travels on a surface vertical to the winding axis in FIG. 1D.

It can be found that although an approximately constant reception strength can be obtained as to a horizontal polarized wave of a radio wave radiated from the coil antenna 1002 regardless of a mutual position between the coil antenna 1002 and the dipole antenna 1003 as shown in FIG. 1C, a reception strength is outstandingly deteriorated (or reduced to 0) as to a vertical polarized wave when the dipole antenna 1003 is positioned in a horizontal direction to the coil antenna 1002 as shown in FIG. 1A. It can be found from what is described above that although the coil antenna does not have directionality as to the horizontal polarized wave, the coil antenna has directionality as to the vertical polarized wave.

Accordingly, in a medical system, which uses a coil antenna as a transmission/receiving antenna of a capsule type medical apparatus and uses a dipole or loop antenna as a transmission/receiving antenna of an external machine as in a conventional medical system, the transmission/receiving sensitivity is deteriorated depending on a positional relation between the antenna of the capsule type medical apparatus and the antenna of the external machine and data may not be accurately transmitted and received between the capsule type medical apparatus and the external machine.

SUMMARY OF THE INVENTION

A medical system according to an aspect of the present invention includes a capsule type medical apparatus that is introduced into a subject and includes a first antenna which outputs a radio wave having directionality in a first polarized wave direction and a first communication unit which executes a communication through the first antenna; an external antenna that is disposed outside of the subject and includes a second antenna having directionality to a second polarized wave direction and a third antenna that is disposed together with the second antenna and has directionality to a third polarized wave direction different from the second polarized wave direction of the second antenna; and an external machine that includes a selection unit which selects any of the second and third antennas and a second communication unit which executes a communication with the first communication unit through the external antenna whose polarized wave surface is selected by the selection unit.

A medical system according to another aspect of the present invention includes a capsule type medical apparatus including a first antenna that is introduced into a subject and outputs a radio wave having directionality in a first polarized wave direction and a first communication unit that executes a communication through the first antenna; an external antenna that is disposed outside of the subject and includes a second antenna having directionality to a second polarized wave direction and a third antenna that is disposed together with the second antenna and has directionality to a third polarized wave direction different from the second polarized wave direction of the second antenna; a sensor that detects a tilt angle of the external antenna to the ground surface; and an external machine that includes a selection unit which selects any of the second and third antennas in response to the tilt angle detected by the sensor and a second communication unit which executes a communication with the first communication unit through the external antenna whose polarized wave surface is selected by the selection unit.

An antenna changeover method according to still another aspect of the present invention is an antenna changeover method for a medical system that includes a capsule type medical apparatus including a first antenna that is introduced into a subject and outputs a radio wave having directionality in a first polarized wave direction and a first communication unit that executes a communication through the first antenna, an external antenna that is disposed outside of the subject and includes a second antenna having directionality to a second polarized wave direction and a third antenna that is disposed together with the second antenna and has directionality to a third polarized wave direction different from the second polarized wave direction of the second antenna, and an external machine that includes a second communication unit which executes a communication with the first communication unit through the external antenna. The antenna changeover method includes a first polarized wave surface selection step of sequentially selecting any of the second and third antennas of the external antenna; a reception strength detection step of detecting reception intensities in the antennas sequentially selected at the first polarized wave surface selection step, respectively; and a second polarized wave surface selection step of selecting an antenna from which a largest reception strength of the reception intensities detected by the reception strength detection step is obtained.

An antenna changeover method according to still another aspect of the present invention is an antenna changeover method for a medical system that includes a capsule type medical apparatus including a first antenna that is introduced into a subject and outputs a radio wave having directionality in a first polarized wave direction and a first communication unit that executes a communication through the first antenna, an external antenna that is disposed outside of the subject and includes a second antenna having directionality to a second polarized wave direction and a third antenna that is disposed together with the second antenna and has directionality to a third polarized wave direction different from the second polarized wave direction of the second antenna, and an external machine that includes a second communication unit which executes a communication with the first communication unit through the external antenna. The antenna changeover method includes a first polarized wave surface selection step of selecting any of the second and third antennas of the external antenna; a first reception strength detection step of detecting a reception strength in the antenna selected in the first polarized wave surface selection step; a determination step of determining whether or not the reception strength detected at the first reception strength detection step satisfies a preset reference value; a second polarized wave surface selection step of sequentially selecting, when the reception strength does not satisfy the reference value as a result of the determination step, any of the second and third antennas of the external antenna; a second reception strength detection step of detecting reception intensities in the antennas sequentially selected at the second polarized wave surface selection step, respectively; and a third polarized wave surface selection step of selecting an antenna from which a largest reception strength of the reception intensities detected by the second reception strength detection step is obtained.

An antenna changeover method according to still another aspect of the present invention is an antenna changeover method for a medical system that includes a capsule type medical apparatus including a first antenna that is introduced into a subject and outputs a radio wave having directionality in a first polarized wave direction and a first communication unit that executes a communication through the first antenna, an external antenna that is disposed outside of the subject and includes a second antenna having directionality to a second polarized wave direction and a third antenna that is disposed together with the second antenna and has directionality to a third polarized wave direction different from the second polarized wave direction of the second antenna, and an external machine that includes a second communication unit which executes a communication with the first communication unit through the external antenna. The antenna changeover method includes a detection step of detecting a tilt angle of the external antenna to the ground surface; and a polarized wave surface selection step of selecting any of the second and third antennas of the external antenna in response to the tilt angle of the external antenna detected at the detection step.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a schematic view showing a schematic configuration of a medical system according to a first embodiment of the invention;

FIG. 9A is an upper view showing a schematic configuration of an external antenna according to a second embodiment of the invention;

FIG. 22 is a schematic view showing a schematic configuration of the medical system according to the second embodiment of the invention.

DETAILED DESCRIPTION OF THE PREFERRED EMBODIMENTS

Figure 1A:
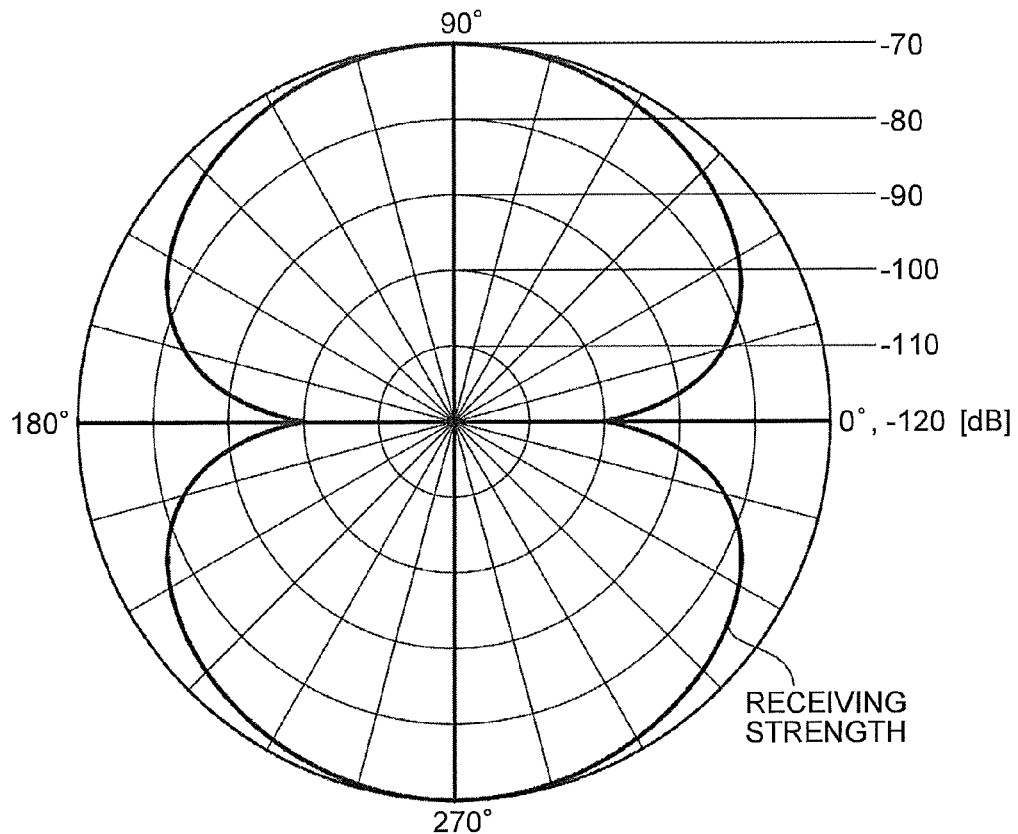
FIG. 1A is a view showing a reception strength position dependence to a vertical polarized wave when a coil antenna is disposed so that a winding axis is vertical to the ground surface.
Figure 1B:
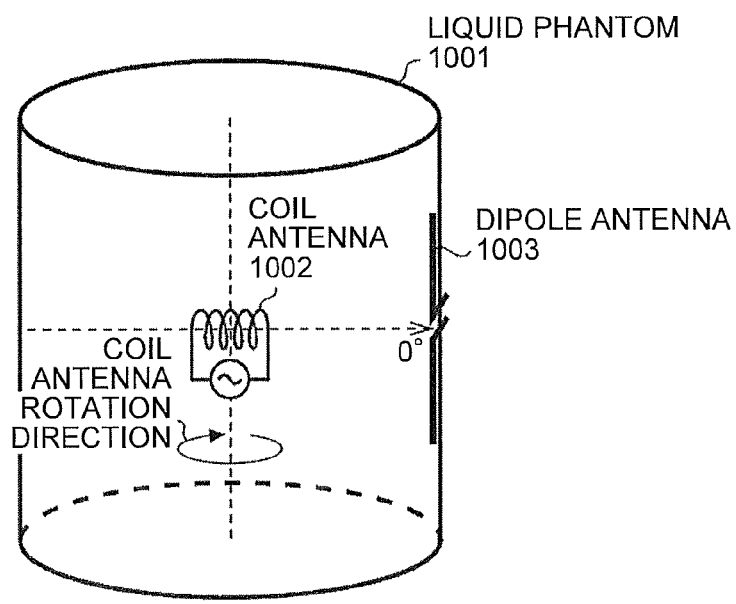
FIG. 1B is a conceptual view showing a positional relation between a transmission antenna (coil antenna) and a reception antenna (dipole antenna) to explain the reception strength position dependence of FIG. 1A.
Figure 1C:
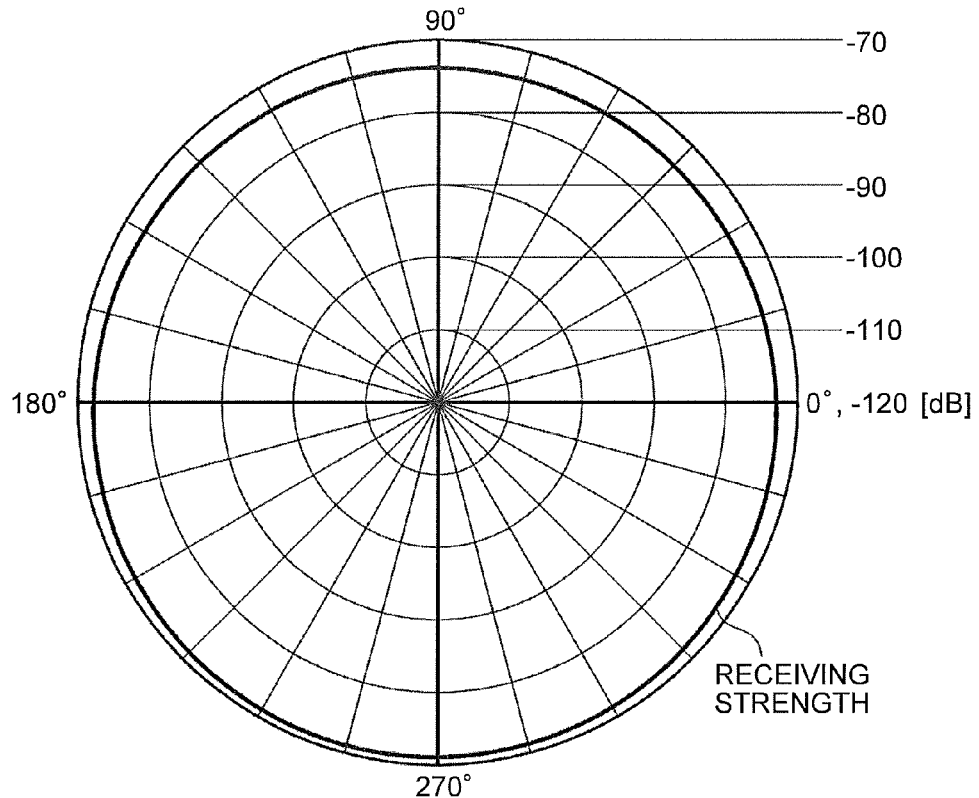
FIG. 1C is a view showing a reception strength position dependence to a horizontal polarized wave when the coil antenna is disposed so that the winding axis is vertical to the ground surface.
Figure 1D:
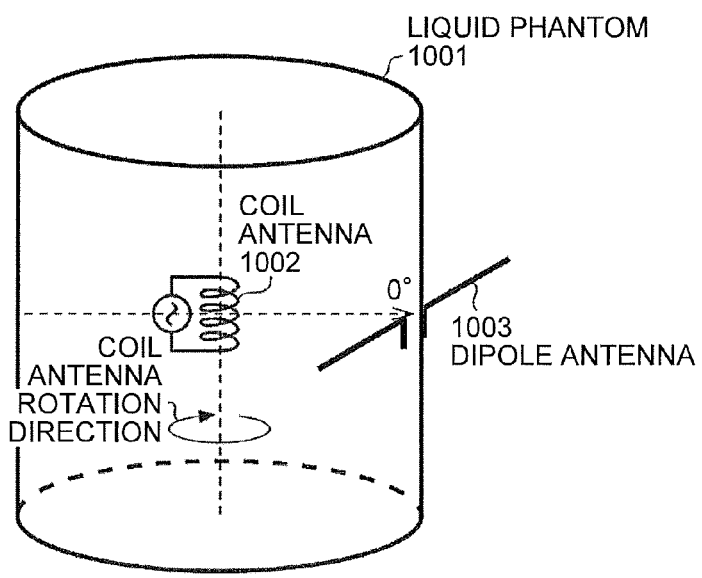
FIG. 1D is a conceptual view showing a positional relation between the transmission antenna (coil antenna) and the reception antenna (dipole antenna) to explain the reception strength position dependence of FIG. 1O.

Best modes for carrying out the invention will be explained below in detail with reference to the drawings. Note that, in the following explanation, the respective drawings only schematically show shapes, sizes, and positional relations in a degree by which the contents of the invention can be understood. Accordingly, the invention is by no means limited only to the shapes, the sizes, and the positional relations exemplified in the respective drawings. Further, in the respective drawings, hatchings in cross sections are partially omitted to clearly show configurations.

First Embodiment

First, a configuration and an operation of a medical system 1 according to a first embodiment of the invention will be explained in detail with reference to the drawings. Note that the embodiment will be explained exemplifying a case that an inner wall image of a stomach 102 is obtained using a capsule type medical apparatus 10 which floats on a liquid 104 stored in the stomach 102. However, the invention is not limited to the case and can be applied also to a capsule type medical apparatus for obtaining some kind of information in a subject 100 while moving from an esophagus to an anus. Further, in-subject information obtained by the capsule type medical apparatus 10 is not limited to a captured image and may be various information such as an in vivo pH value, a cell tissue, a blood, a body fluid, and the like. Further, a body part in which the liquid 104 is stored is not limited to the stomach 102 and may be various organs, for example, a small intestine, a large intestine, and the like. Further, liquids, for example, normal saline, water, and the like, which do not adversely affect the subject 100 and the capsule type medical apparatus 10, are preferably used as the liquid 104. Note that the liquid 104 is preferably transparent. As a result, it can be avoided that a captured image is made unclear by the liquid 104 when an in-subject image is obtained as, for example, in-subject information.

FIG. 2 is a schematic view showing a schematic configuration of the medical system 1 according to the embodiment. As shown in FIG. 2, the medical system 1 includes the capsule type medical apparatus 10, which floats on the liquid 104 introduced into the subject 100, for example, orally and stored in the stomach 102, and an external machine 30 for transmitting and receiving image data, a control command, and the like between it and the capsule type medical apparatus 10 by executing a wireless communication with the capsule type medical apparatus 10. An external antenna 20 is connected to the external machine 30 through connection cables 39, and the external machine 30 and the capsule type medical apparatus 10 execute a wireless communication using the external antenna 20. Note that although the external machine and the external antenna are explained separately in the following explanation, the invention is not limited to the configuration and the external antenna and the external machine may be configured as one external device.

Further, the external machine 30 may be configured so that, for example, it can execute a wireless/wired communication with an operation terminal 60 to which the operator inputs various kinds of operations such as an imaging instruction and the like. Further, the external machine 30 may be configured so that it can be connected to an information processing terminal 50 such as a personal computer, a workstation, and the like through a communication cable 59, for example, a USB (Universal Serial Bus) cable and a LAN (Local Area Network) cable. Further, the external machine 30 may be configured so that an external storage medium such as a portable storage medium 40 and the like can be attached thereto. Further, the external machine 30 may be configured so that a display device such as a liquid crystal display and the like can be connected thereto through, for example, a not shown monitor cable. Note that the external machine 30 itself may be provided with an input unit for inputting various kinds of operations, a storage unit such as an EEPROM (Electrically Erasable Programmable Read Only Memory) and the like, and a display unit such as a liquid crystal display and the like.

Capsule Type Medical Apparatus

Figure 3:
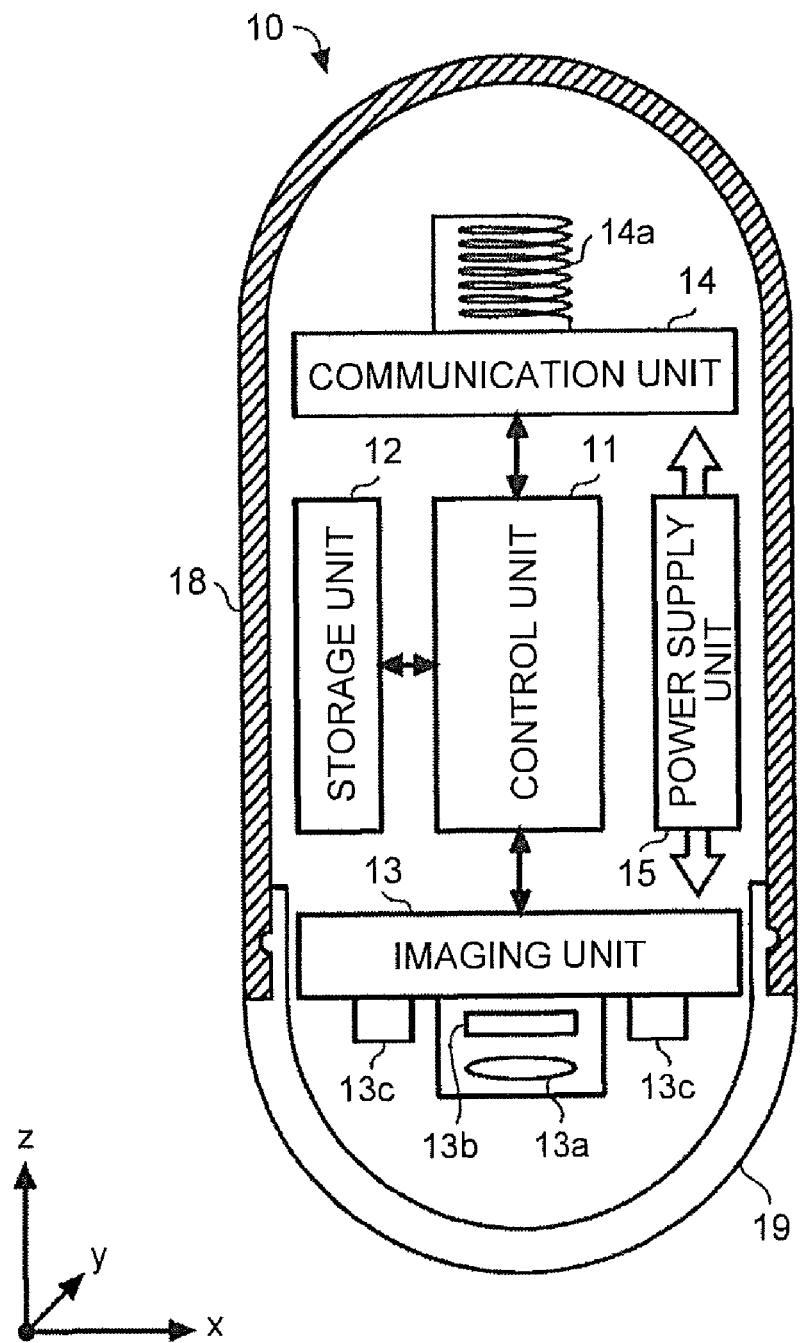
FIG. 3 is a schematic view showing a schematic configuration of a capsule type medical apparatus according to the first embodiment of the invention.

Here, an example of the capsule type medical apparatus 10 according to the embodiment will be explained in detail with reference to the drawings. FIG. 3 is a schematic view showing a schematic configuration of the capsule type medical apparatus 10 according to the embodiment. As shown in FIG. 3, the capsule type medical apparatus 10 includes an imaging unit 13 for obtaining an image in, for example, the subject 100, a communication unit 14 for executing a wireless communication with the external machine 30, a control unit 11 for controlling respective portions (units) in the capsule type medical apparatus 10 such as the imaging unit 13, the communication unit 14, and the like, a storage unit 12 for storing image data of an in-subject image obtained by the imaging unit 13, various kinds of data such as a control command and the like received through the communication unit 14, various kinds of programs and the like executed by the control unit 11 to control the respective portions in the capsule type medical apparatus 10, and a power supply unit 15 for supplying power to the respective portions in the capsule type medical apparatus 10.

The control unit 11 realizes various kinds of operations such as an imaging operation and a transmission/receiving operation in the respective portions by controlling/driving the respective portions (units) in the capsule type medical apparatus 10 based on various kinds of control programs read from, for example, the storage unit 12 and on the control command and the like received from the external machine 30 through the communication unit 14. The control unit 11 can be configured using an information processing device, for example, a CPU (Central Processing Unit), an MPU (Microprocessor), and the like.

The storage unit 12 stores various kinds of control programs appropriately executed by the control unit 11, image data obtained by the imaging unit 13, various kinds of data received through the communication unit 14, other configuration information, and the like. The storage unit 12 can be configured using, for example, a RAM (Random Access Memory) and the like. Further, the storage unit 12 may include a ROM (Read Only Memory) for storing the various kinds of control programs described above. Further, the storage unit 12 may store not only the various kinds of data, the other configuration information, and the like but also image data received from the capsule type medical apparatus 10.

The imaging unit 13 has such a configuration that it is mounted on a circuit board on which, for example, an imaging unit 13a for obtaining an image in the subject 100 as image data, an optical lens 13b disposed on a light receiving surface side of the imaging unit 13a, and at least one illumination 13c for illuminating inside of the subject 100 when an image is captured have a predetermined drive/control circuit, wirings, and the like. The imaging unit 13 appropriately obtains an in-subject image (inner wall image of the stomach 102) as image data by operating under a control from the control unit 11. The obtained image data is recorded in the storage unit 12 through, for example, the control unit 11 or sent to the external machine 30 from the communication unit 14. Note that a CCD (Charge Coupled Device) camera, a CMOS (Complementary Metal Oxide Semiconductor) camera, and the like, for example, can be used as the imaging unit 13a. Further, an LED (Light Emitting Diode), for example, can be used as the illumination 13c. Note that the capsule type medical apparatus 10 may include plural imaging units 13.

The communication unit 14 for realizing a communication means (first communication unit) using an antenna 14a has such a configuration that the antenna 14a is mounted on a circuit board having a predetermined transmission/receiving circuit, wirings, and the like, appropriately transmits the image data obtained by the imaging unit 13 or the image data stored in the storage unit 12 to the external machine 30 by operating under the control from the control unit 11, and further receives the various kinds of data such as the control command and the like transmitted from the external machine 30 and inputs the various kinds of data to the control unit 11. Note that, in the embodiment, a coil antenna (also called a loop antenna) for outputting a radio wave, in which at least one of a vertical polarized wave and a horizontal polarized wave has directionality, is used as the antenna 14a (first antenna). This is because the coil antenna has a large gain in a small antenna. However, the invention is not limited to the coil antenna and, for example, various antennas can be used.

Further, the respective portions described above are accommodated in a capsule type vessel (casing) composed of an approximately cylindrical or semi-oval spherical main vessel (first casing) 18 having one end formed in a hemispherical dome shape and the other end opened and a hemispherical sub vessel (second casing) 19 for sealing inside of the main vessel 18 by being engaged with the opening of the main vessel 18. The capsule type vessels (18, 19) have such a degree of size that, for example, the subject 100 can swallow the vessels. Further, in the embodiment, at least the sub vessel 19 is formed of a transparent material as well as the imaging unit 13 described above is disposed to the sub vessel 19 side facing an external direction. With this configuration, the imaging unit 13 can capture the inner wall of the stomach 102 through the transparent sub vessel 19. Note that the main vessel 18 may be formed in an approximately cylindrical shape having both ends opened, and the inside of the main vessel 18 may be sealed by engaging the sub vessels 19 formed of the transparent material with the two openings, respectively. In this case, the capsule type medical apparatus 10 can mount the imaging units 13 to both of the ends, respectively. Note that the respective imaging units 13 are disposed facing the external directions.

In addition to the configuration described above, the capsule type medical apparatus 10 according to the embodiment is configured such that an overall specific gravity becomes smaller than a specific gravity of the liquid 104. As a result, the capsule type medical apparatus 10 can be caused to float on a liquid surface of the liquid 104 stored in the stomach 102. However, the specific gravity of the capsule type medical apparatus 10 is not necessarily smaller than the specific gravity of the liquid 104.

Further, a center of gravity of the capsule type medical apparatus 10 is offset from centers of the overall capsule type vessels (18, 19) so that the capsule type medical apparatus 10 keeps its posture (a posture to, for example, the ground surface) constant regardless of a posture of the subject 100 in the stomach 102 of the subject 100. In the embodiment, when the ground surface is, for example, an xy plane in FIG. 3, the center of gravity of the capsule type medical apparatus 10 is offset so that a longitudinal direction of the capsule type medical apparatus 10 floating on the liquid 104 keeps, for example, a z-direction as well as the sub vessel 19, which forms an imaging window, is positioned on a lower side.

The offset of the center of gravity can be realized by disposing a member having a large specific gravity on the sub vessel 19 side in, for example, an internal configuration. Since, for example, a button battery and the like used as the power supply unit 15 have a large specific gravity in comparison with the other configurations, when the button battery and the like are disposed on the sub vessel 19 side, the center of gravity of the capsule type medical apparatus 10 can be offset to the sub vessel 19 side. Note that it is needless to say that the center of gravity can be offset by various configurations, for example, offsetting an overall internal configuration to the sub vessel 19 side and the like.

As described above, a direction of the antenna 14a of the communication unit 14 can be restricted by configuring the capsule type medical apparatus 10 so that the posture of the capsule type medical apparatus 10 floating on the liquid 104 is kept in a predetermined direction. Thus, in the embodiment, as shown in, for example, FIG. 3, the antenna 14a is fixed in the capsule type medical apparatus 10 (for example, on the circuit board of the communication unit 14) so that a winding axis of the antenna 14a is vertical (z-direction) to the liquid surface (the ground surface, that is, the xy plane). With this configuration, since the capsule type medical apparatus 10 is configured to receive the horizontal polarized wave using an external antenna 20 to be described later even when the subject 100 takes any posture, it can be prevented that a reception efficiency is lowered by a body position of the subject 100. Further, since the horizontal polarized wave has such characteristics that a reflection loss is small on a boundary surface between a liquid (for example, the liquid 104) and a gas (for example, a gas in the stomach 102), a radio wave from the capsule type medical apparatus 10 can be received more efficiently by configuring the horizontal polarized wave so that it can be received regardless of the body position of the subject 100. Note that a relation among the direction of the antenna 14a, the posture of the subject 100, and the external antenna 20 will be described later.

Further, it is sufficient that the specific gravity of the capsule type medical apparatus 10 has such a degree of specific gravity that at least a part of the capsule type medical apparatus 10 projects on the liquid surface of the liquid 104.

External Antenna

Figure 4A:
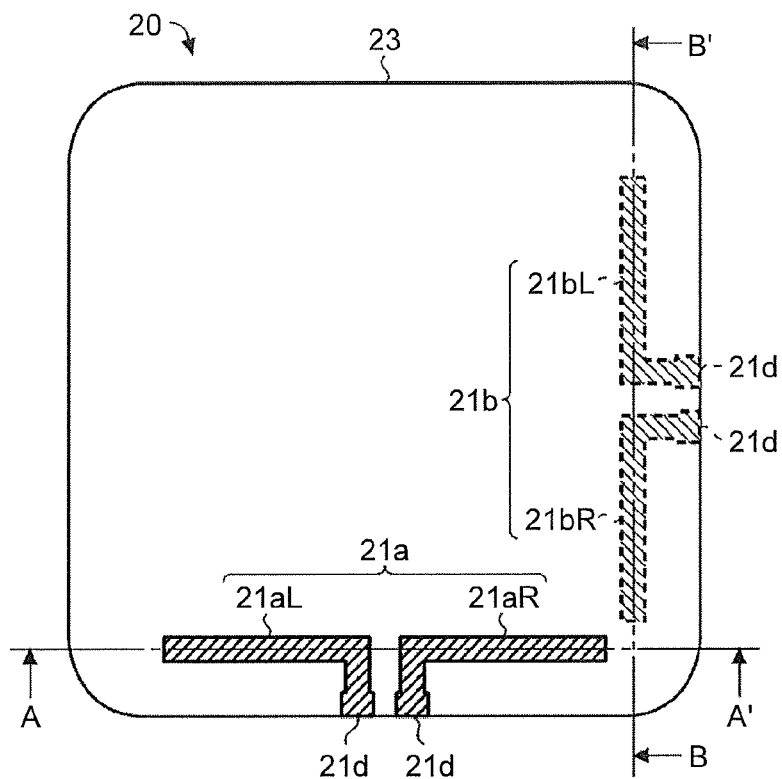
FIG. 4A is an upper view showing a schematic configuration of an external antenna according to the first embodiment of the invention.
Figure 4B:
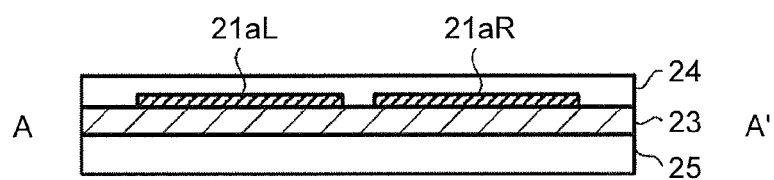
FIG. 4B is an A-A' sectional view of FIG. 4A.
Figure 4C:
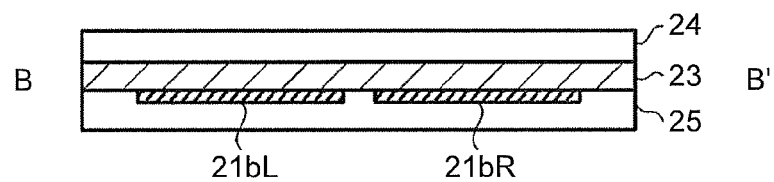
FIG. 4C is a B-B' sectional view of FIG. 4A.

Next, an example of the external antenna 20 according to the embodiment will be explained in detail with reference to the drawings. FIGS. 4A to 4C are schematic views showing a schematic configuration of the external antenna 20 according to the embodiment. Note that FIG. 4A is an upper view of the external antenna 20, FIG. 4B is an A-A' sectional view of FIG. 4A, and FIG. 4C is a B-B' sectional view of FIG. 4A. Further, in FIG. 4A, a cover film 24 for protecting an antenna portion is omitted to clarify explanation.

As shown in FIG. 4A, the external antenna 20 has a configuration in which two dipole antennas 21a and 21b are formed on front/back surfaces of an approximately square flexible board 23. However, the invention is not limited to the dipole antennas and can use various antennas, for example, loop antennas, micro strip antennas (also referred to as patch antennas), and the like.

The dipole antenna 21a includes two elements 21aL and 21aR disposed symmetrically. In contrast, the dipole antenna 21b includes two elements 21bL and 21bR disposed symmetrically likewise. Electrode pads 21d are disposed to the respective elements 21aL, 21aR, 21bL and 21bR to electrically guide them to an end of the flexible board 23.

Further, the dipole antenna 21a (second antenna) and the dipole antenna 21b (third antenna) are disposed so that extending directions of the respective elements of them are orthogonal to each other. With this configuration, in the embodiment, since the external antenna 20 is configured to have plural different polarized wave surfaces, even when the external antenna 20 is positioned in a horizontal direction to the capsule type medical apparatus 10, a horizontal polarized wave of a radio wave output from the antenna 14a of the capsule type medical apparatus 10 can be received using any of the dipole antennas (21a or 21b). As a result, the radio wave from the capsule type medical apparatus 10 can be efficiently received regardless of a body position of the subject 100.

As shown in FIG. 4B, the dipole antenna 21a is formed on, for example, one of main surfaces (which is a front surface) of the flexible board 23. In contrast, as shown in FIG. 4C, the dipole antenna 21b is formed on, for example, the other main surface (which is a back surface) of the flexible board 23. However, the dipole antennas 21a, 21b are not limited to the above configurations, and both of the dipole antennas 21a, 21b may be formed on the same surface and on the same layer of the flexible board 23.

Further, as shown in FIG. 4B or in FIG. 4C, the front surface of the flexible board 23 on which the dipole antennas 21a and 21b are formed is covered with the cover film 24 to protect the dipole antenna 21a formed on the flexible board 23. In contrast, an adhesive film 25 for attaching the external antenna 20 to the subject 100 is formed on the back surface of the flexible board 23. The adhesive film 25 also plays a role for protecting the dipole antenna 21b formed on the back surface of the flexible board 23. However, the external antenna 20 is not limited to the above configuration and may be configured to be attached to, for example, clothing such as a jacket and the like. In this case, when the external antenna 20 is detachably attached to the clothing, various configurations such as a magic tape (registered trademark) and the like can be used.

Here, a film-like board, which is composed of a material having a plastic property and further having the same dielectric constant as a dielectric constant of the subject 100, is preferably used as the flexible board 23. Likewise, a material having a plastic property and further having the same dielectric constant as the dielectric constant of the subject 100 is preferably used as the adhesive film 25 disposed between the dipole antennas 21a and 21b and the capsule type medical apparatus 10. However, "the same dielectric constant" referred to in the invention may not necessarily the same and may be a dielectric constant capable of reducing a reflection of a radio wave from the antenna 14a in such a degree that "the same dielectric constant" can be regarded as large as the dielectric constant of the subject 100. With this configuration, since the flexible board 23 can be caused to come into intimate contact with the subject 100 using the adhesive film 25 as well as a reflection of the radio wave by the flexible board 23 and/or the adhesive film 25 can be suppressed, a stronger reception strength can be obtained. Further, when the external antenna 20 is attached to the clothing such as the jacket and the like, the clothing is preferably formed of a material having the same dielectric constant as the dielectric constant of the subject 100.

Note that, in the embodiment, although a case that the dipole antennas 21a and 21b, which are orthogonal to each other, are formed on the front/back surfaces of the single layer flexible board 23 is exemplified, the invention is not limited thereto, and the dipole antennas 21a and 21b may be formed on any of the same or different layers of a flexible board having, for example, a layered structure.

External Machine

Figure 5:
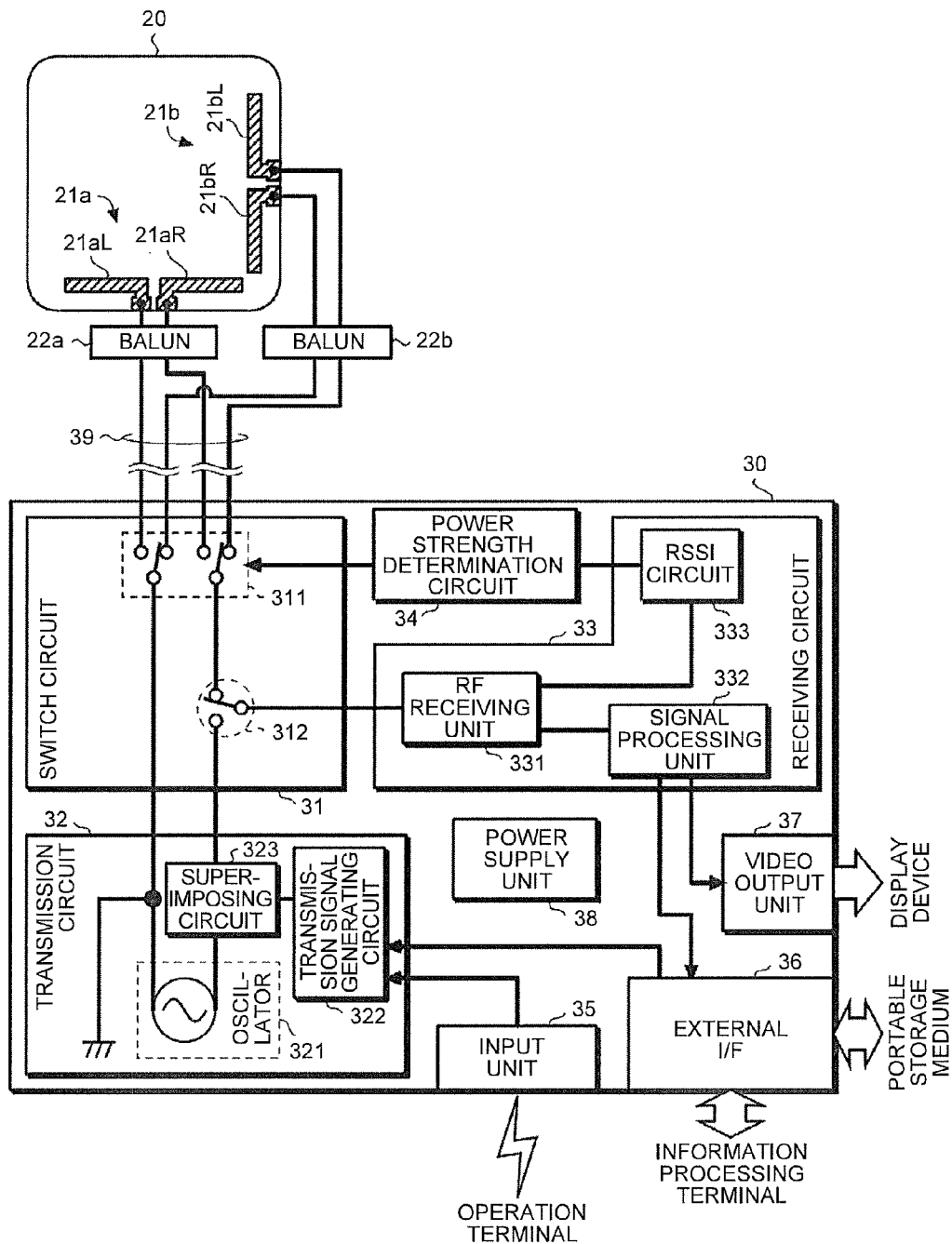
FIG. 5 is a schematic view showing a schematic configuration of an external machine according to the first embodiment of the invention.

Next, an example of the external machine 30 according to the embodiment will be explained in detail with reference to the drawings. FIG. 5 is a schematic view showing a schematic configuration of the external machine 30 according to the embodiment. As shown in FIG. 5, the external machine 30 includes a switch circuit 31 for switching an antenna configuration and a transmission/receiving of the external antenna 20, a transmission circuit 32 for creating a transmission signal in which various kinds of data such as an input control command and the like are superimposed in a predetermined transmission frequency, an input unit 35 for inputting the various kinds of data such as the control command and the like input from the operation terminal 60 (refer to FIG. 2) to the transmission circuit 32, a receiving circuit 33 for reproducing a reception signal input through the external antenna 20 to a data signal, a power strength determination circuit 34 for determining a power strength of a radio wave received by the external antenna 20, a video output unit 37 for converting image data of the data signal reproduced by the receiving circuit 33 to video data to be displayed on an external display device and outputting the video data, an external interface (I/F) 36 for controlling a connection to the information processing terminal 50 (refer to FIG. 2) and the portable storage medium 40 (refer to FIG. 2), and a power supply unit 38 for supplying power to the respective portions.

In the above configuration, the switch circuit 31 includes an antenna changeover switch 311 for changing over an antenna to be used as any of the two dipole antennas 21a and 21b of the external antenna 20 and a transmission/receiving changeover switch 312 for changing over a connection destination in the external machine 30 of the external antenna 20.

The antenna changeover switch 311 is composed of at least two 2-way switches configured using, for example, plural switching transistors, and change-over terminals of the respective 2-way switches are appropriately connected to the electrode pads 21d of the respective elements (21aL or 21bL, and, 21aR or 21bR) of the dipole antennas 21a and 21b through the connection cables 39 and baluns 22a, 22b. The antenna changeover switch 311 changes over the antenna to be used as any of the two dipole antennas 21a and 21b disposed to the external antenna 20 based on a control signal output from the power strength determination circuit 34 to be described later. With this operation, any of the plural polarized wave surfaces of the external antenna 20 can be selected. More specifically, the antenna changeover switch 311 functions as a selection means for selecting any of the plural polarized wave surfaces of the external antenna 20. Further, the balun 22a and 22b, which are equilibrium/non-equilibrium conversion circuits for converting electric signals in equilibrium and non-equilibrium states, are disposed on the connection cables 39 for connecting the respective dipole antennas 21a and 21b and the antenna changeover switch 311.

The transmission/receiving changeover switch 312 is a 2-way switch configured using, for example, plural switching transistors and switches a connection destination of the external antenna 20 to any of the transmission circuit 32 and the receiving circuit 33 in transmission and in reception. The transmission/receiving changeover switch 312 can be configured so that it is controlled by, for example, the power strength determination circuit 34 to be described later, a not shown control unit, and the like.

The transmission circuit 32 includes an oscillator 321 for oscillating in a predetermined transmission frequency based on a not shown reference voltage, a transmission signal generating circuit 322 for creating a transmission signal from the various kinds of data such as the control command and the like input from the input unit 35 and the external I/F 36 or the not shown control unit, and a superimposing circuit 323 for superimposing the transmission signal created by the transmission signal generating circuit 322 to a transmission frequency signal output from the oscillator 321. Accordingly, in transmission, the transmission signal is superimposed in the superimposing circuit 323 to the oscillation frequency signal output from the oscillator 321, and thereafter the transmission frequency signal, to which the transmission signal is superimposed, is input to the external antenna 20 through the switch circuit 31 and transmitted to the external capsule type medical apparatus 10 as a radio wave signal from any of the dipole antenna 21a or 21b of the external antenna 20.

The receiving circuit 33 includes an RF receiving unit 331 for reproducing data sent from the capsule type medical apparatus 10 by subjecting a frequency signal input from the external antenna 20 through the switch circuit 31 to filtering, down convert, demodulation, decode, and the like and for outputting reception data, a signal processing unit 332 for executing a predetermined processing using the reception data output from the RF receiving unit 331, and an RSSI (Received Signal Strength Indicator) circuit 333 for creating a signal (strength index signal) showing a strength index of the reception radio wave based on an IF (Intermediate Frequency) signal obtained by executing the down convert in the RF receiving unit 331.

As described above, at least one of the transmission circuit 32 and the receiving circuit 33 functions as a communication means (second communication unit) for executing a communication with the capsule type medical apparatus 10 through the dipole antenna (21a or 21b) selected by the antenna changeover switch 311.

Note that after the reception data, which is reproduced by the RF receiving unit 331, is subjected to a predetermined processing such as pixel interpolation and the like in, for example, the signal processing unit 332, the reception data is sent to the information processing terminal 50 (refer to FIG. 2) connected through the external I/F 36 or recorded in an external storage medium such as the portable storage medium 40 (refer to FIG. 2) attached to the external I/F 36, and the like. Further, when the reception data is image data, the image data can also be directly displayed on a display device such as a liquid crystal display and the like by providing a video output unit 37 as shown in FIG. 5.

As described above, the RSSI circuit 333 creates the strength index signal showing the strength index of the reception radio wave based on an IF signal obtained by executing the down convert in the RF receiving unit 331. The created strength index signal is input to the power strength determination circuit 34 to be described later.

The power strength determination circuit 34 can be configured using, for example, an information processing circuit such as an MPU and the like, a comparison circuit including an operation amplifier, and the like. The power determination circuit 34 outputs a control signal for causing the antenna changeover switch 311 to select the dipole antenna (21a or 21b) which is used for the communication based on the strength index signal input from the RSSI circuit 333. The control signal can be configured as, for example, a binary (for example, 1 bit) voltage signal. Further, when the power determination circuit 34 is composed of the information processing circuit such as the MPU and the like, a comparison of two strength index signals can be realized by a configuration for disposing a quantization circuit for quantizing the strength index signals to an input stage and comparing values obtained by it.

As described above, the RSSI circuit 333 and the power strength determination circuit 34 function as a reception strength detection means for detecting a reception strength by the dipole antenna (21a or 21b) selected by the antenna changeover switch 311.

Here, an operation when the dipole antenna (21a or 21b) used in transmission/receiving is selected will be explained in detail. Note that the operation is realized by that, for example, the power strength determination circuit 34, the not shown control unit, and the like control respective circuits in the external machine 30. In the following explanation, a case that the power strength determination circuit 34 controls the respective circuits will be exemplified.

In an operation in transmission/receiving, first, any of the dipole antennas (for example, the dipole antenna 21a) is connected to the transmission/receiving changeover switch 312 based on an output from the power strength determination circuit 34. At the time, the transmission/receiving changeover switch 312 connects the antenna changeover switch 311 to the transmission circuit 32 according to a control voltage from, for example, an electrode strength determination circuit 34. Thus, the electrode strength determination circuit 34 causes the transmission signal generating circuit 322 in the transmission circuit 32 to create a control command for outputting a signal for measuring a strength of the reception radio wave (hereinafter, referred to as a reception strength measuring signal) and transmits it to the capsule type medical apparatus 10 through the dipole antenna 21a. Thereafter, the electrode strength determination circuit 34 places the antenna changeover switch 311 and the receiving circuit 33 in a connected state by controlling the transmission/receiving changeover switch 312. Note that the capsule type medical apparatus 10 may output the reception strength measuring signal at predetermined intervals without transmitting the control command. In this case, the transmission circuit 32 need not be operated in a power strength determination.

In contrast, the capsule type medical apparatus 10 outputs the reception strength measuring signal from the antenna 14a for a predetermined time (or a predetermined number of times at predetermined intervals) according to the received control command. The reception strength measuring signal is received by the dipole antenna 21a of the external antenna 20. With this operation, the strength index signal as to a radio wave received by the dipole antenna 21a is input to the power strength determination circuit 34 from the RSSI circuit 333.

When the strength index signal as to the radio wave received by the dipole antenna 21a is input, a control signal for switching a connection destination of the antenna changeover switch 311 to the dipole antenna 21b is output from the power strength determination circuit 34. With this operation, the strength index signal as to a radio wave received by the dipole antenna 21b is input to the power strength determination circuit 34 from the RSSI circuit 333. Note that, during a period until at least the operation is completed, the reception strength measuring signal is output from the capsule type medical apparatus 10.

When all the dipole antennas (21a and 21b in the example) are scanned and the respective strength index signals are input as described above, the power strength determination circuit 34 compares reception intensities obtained by the respective strength index signals. In the example, a value of the strength index signal as to the radio wave, which is input first and received by the dipole antenna 21a, is compared with a value of the strength index signal as to the radio wave received by the dipole antenna 21b (for example, a voltage value integrated by a predetermined time constant). The power strength determination circuit 34 outputs a control signal showing that the reception strength of which of the dipole antenna (21a or 21b) is larger based on a result of the comparison. With this operation, the antenna changeover switch 311 operates to select the dipole antenna (21a or 21b) having the larger reception strength.

Further, although the above operation is executed so that the respective reception intensities of the plural dipole antennas (21a and 21b) are detected and a dipole antenna having the strongest reception strength is selected, the invention is not limited thereto. The dipole antenna having the strongest reception strength may be selected by executing the above operation when, for example, the reception strength by the dipole antenna selected first (the dipole antenna 21a in the example described above) is smaller than a preset reference value.

In addition to the above mentioned configuration, when the control command and the like are input from the operation terminal 60 through, for example, a wired line, the input unit 35 can be composed of a USB interface and the like, and when the control command and the like are input from the operation terminal 60 through a wireless line of, for example, infrared rays, a short wave, a long wave, and the like, the input unit 35 can be composed of an infrared ray receiving device, a short/long wave receiving device, and the like. Further, when, for example, the portable storage medium 40 can be attached to the external I/F 36, the external I/F 36 can be composed of a USB interface and the like, and when the information processing terminal 50 can be connected to the external I/F 36 through the communication cable 59, the external I/F 36 can be composed of a network interface and the like. However, the invention is not limited thereto and can be variously modified.

Positional Relation

Figure 6A:
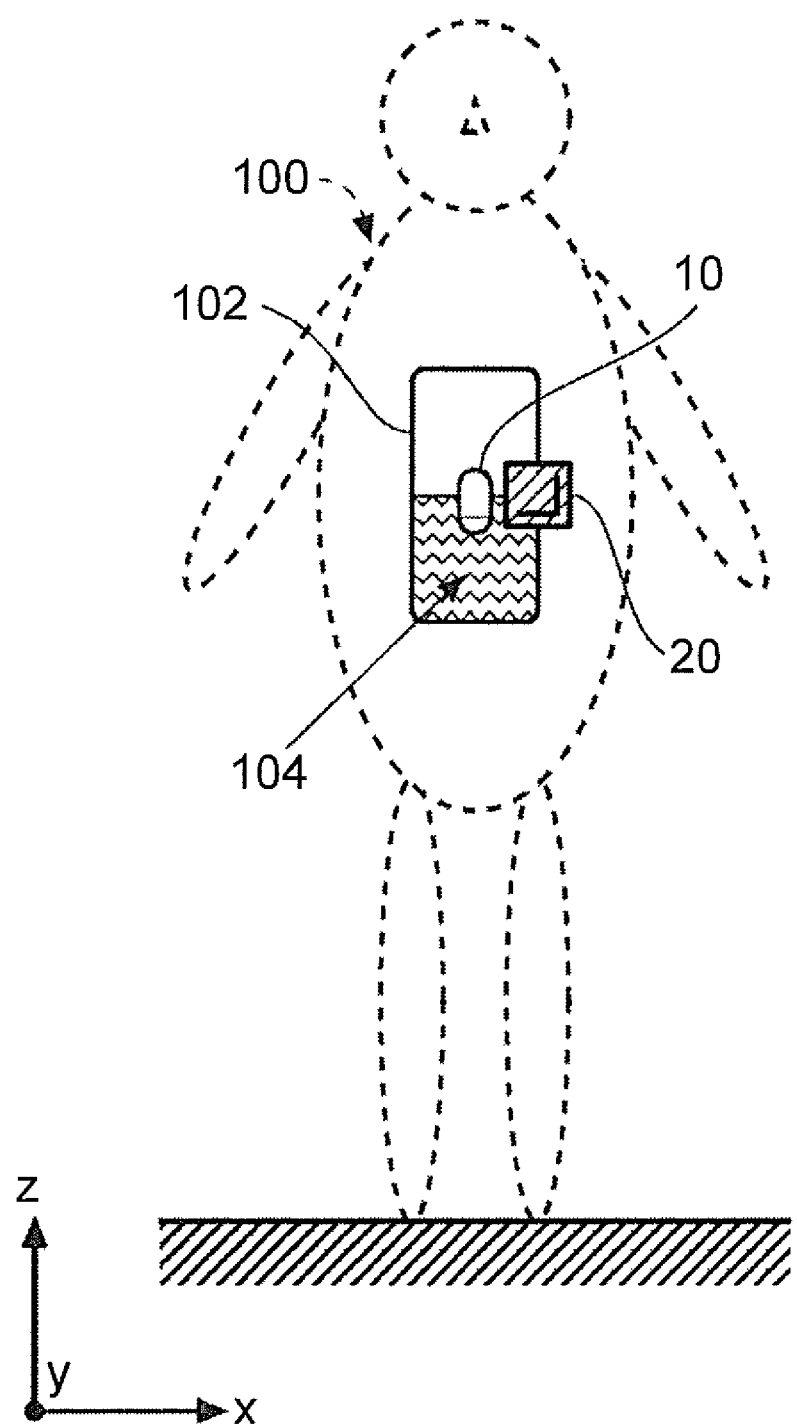
FIG. 6A is a schematic view explaining a positional relation between the capsule type medical apparatus introduced into a stomach of a subject and an external antenna attached to an outside surface of the subject in the first embodiment of the invention (standing position)
Figure 6B:
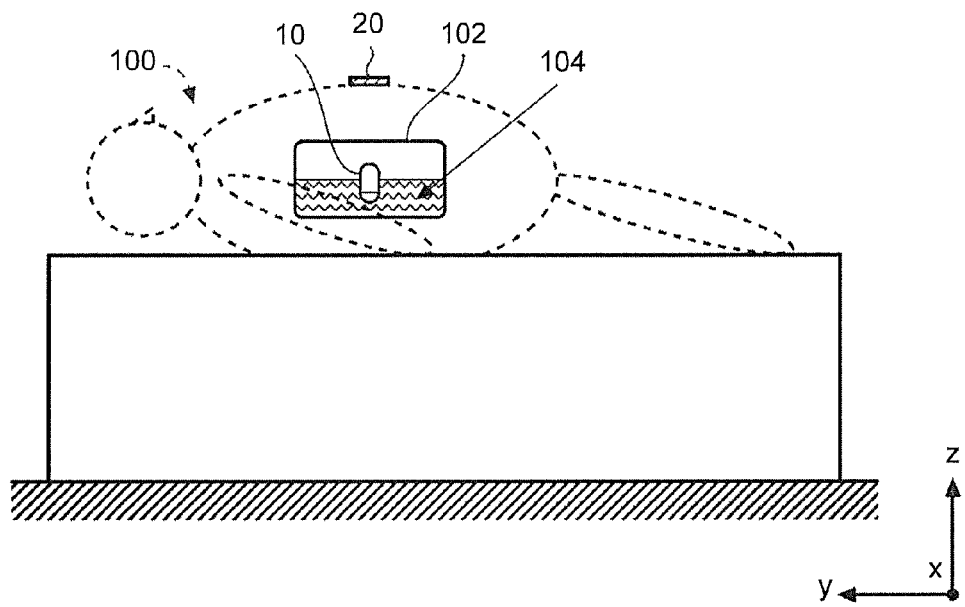
FIG. 6B is a schematic view explaining a positional relation between the capsule type medical apparatus introduced into the stomach of the subject and the external antenna attached to the outside surface of the subject in the first embodiment of the invention (back lying position)
Figure 6C:
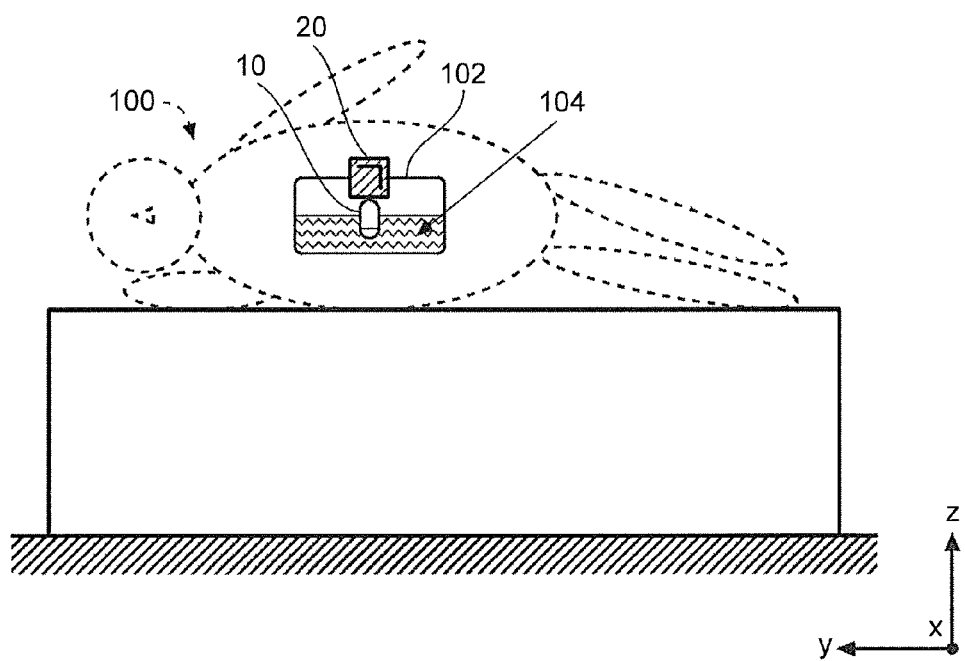
FIG. 6C is a schematic view explaining a positional relation between the capsule type medical apparatus introduced into the stomach of the subject and the external antenna attached to the outside surface of the subject in the first embodiment of the invention (right side lying position)

Next, a relation among a direction of the antenna 14a, a posture of the subject 100, and the external antenna 20 in the embodiment will be explained in detail with reference to the drawings. FIGS. 6A to 6C are schematic views explaining a positional relation between the capsule type medical apparatus 10 introduced into the stomach 102 of the subject 100 and the external antenna 20 attached to an outside surface of the subject 100. Note that, in the following explanation, the external antenna 20 is attached around the trunk of the subject 100. Further, in a state that the subject 100 takes a standing position, the dipole antenna 21a of the external antenna 20 extends in a horizontal direction (direction parallel to the ground surface), and the dipole antenna 21b extends in a vertical direction (direction vertical to the ground surface).

Further, the capsule type medical apparatus 10 in the subject 100 floats while keeping a posture on the liquid surface of the liquid 104 in the stomach 102 as described above. Accordingly, the winding axis of the antenna 14a disposed to the capsule type medical apparatus 10 keeps a predetermined direction at all times regardless of the posture of the subject 100 except an unstable state when the subject 100 changes a body position. In the embodiment, as shown in, for example, FIG. 3, the winding axis of the antenna 14a keeps the vertical direction (z-axis direction) to the ground surface. Accordingly, a vertical polarized wave of a radio wave output from the antenna 14a travels along a surface parallel with the z-axis, and a horizontal polarized wave travels along a surface parallel with the xy plane.

Standing Position (Sitting Position)

First, a case that the subject 100 takes the standing position will be explained. As shown in FIG. 6A, when the subject 100 takes the standing position, the dipole antenna 21a of the external antenna 20 extends in the horizontal direction (x-direction in FIG. 6A) parallel with the ground surface, and the dipole antenna 21b extends in the vertical direction (z-direction in FIG. 6A) to the ground surface. Accordingly, the dipole antenna 21a of the two dipole antennas 21a and 21b receives a horizontal polarized wave of a radio wave radiated from the antenna 14a, and the dipole antenna 21b receives a vertical polarized wave of the radio wave radiated from the antenna 14a. Note that the relation is also the same even when the subject 100 takes a sitting position posture.

Back Lying Position (Belly Lying Position)

Further, when the subject 100 takes a back lying position, as shown in FIG. 6B, the dipole antennas 21a and 21b of the external antenna 20 extend together in the horizontal direction (x-axis direction or y-axis direction in FIG. 6B) parallel with the ground surface. Accordingly, the two dipole antennas 21a and 21b can receive together the horizontal polarized wave of the radio wave radiated from the antenna 14a. Note that the relation is also the same even when the subject 100 takes a belly lying position (face down lying position).

Right Side Lying Position (Left Side Lying Position)

Further, when the subject 100 takes a right side lying position, as shown in FIG. 6C, the dipole antenna 21a of the external antenna 20 extends in the vertical direction (z-axis direction in FIG. 6C) to the ground surface, and the dipole antenna 21b extends in the horizontal direction (y-direction in FIG. 6C) parallel with the ground surface. Accordingly, the dipole antenna 21a of the two dipole antennas 21a and 21b receives the vertical polarized wave of the radio wave radiated from the antenna 14a, and the dipole antenna 21b receives the horizontal polarized wave of the radio wave radiated from the antenna 14a. Note that the relation is also the same even when the subject 100 takes a left side lying position.

As described above, according to the embodiment, since it is possible to configure the external antenna 20 so that the horizontal polarized wave is received using the external antenna 20 even when the subject 100 takes any posture, a reception efficiency can be prevented from being deteriorated by a body position of the subject 100. As a result, data can be accurately transmitted and received between the capsule type medical apparatus 10 and the external machine 30 without depending on a positional relation between the antenna 14a of the capsule type medical apparatus 10 and the external antenna 20 used by the external machine 30.

Modification 1

Figure 7A:
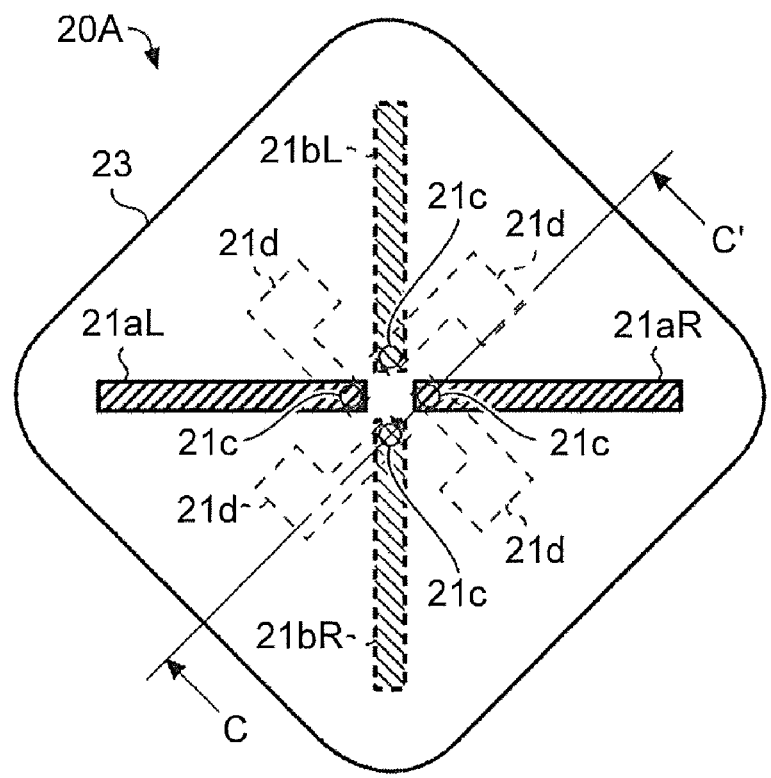
FIG. 7A is an upper view showing a schematic configuration of an external antenna according to a modification 1 of the first embodiment of the invention.
Figure 7B:
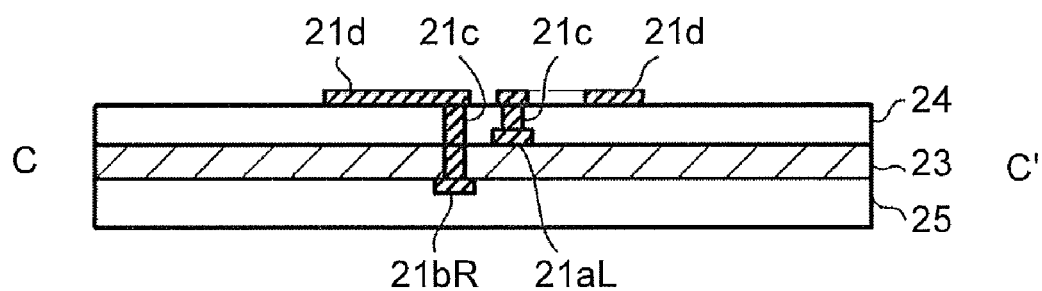
FIG. 7B is a C-C' sectional view of FIG. 7A.

Here, a modification 1 of the external antenna 20 according to the embodiment will be explained in detail with reference to the drawings. FIG. 7A is an upper view showing a schematic configuration of an external antenna 20A according to the modification. Further, FIG. 7B is a C-C' sectional view of FIG. 7A. Note that, in FIG. 7A, the cover film 24 for protecting an antenna portion is omitted to clarify explanation.

As shown in FIG. 7A, the external antenna 20A has such a configuration that elements 21aL and 21aR, which constitute a dipole antenna similar to the dipole antenna 21a of the external antenna 20 are formed on a diagonal line of a front surface of a flexible board 23, and the elements 21bL and 21bR, which constitute the dipole antenna 21b similar to the dipole antenna 21b of the external antenna 20 are formed on a diagonal line of a back surface of the flexible board 23. Note that an antenna composed of the elements 21aL and 21aR and an antenna composed of the elements 21bL and 21bR are disposed orthogonal to each other likewise the external antenna 20.

Further, as shown in FIGS. 7A and 7B, the respective elements 21aL, 21aR, 21bL, and 21bR are electrically connected to the electrode pads 21d on the cover film 24 through via contacts 21c passing through the cover film 24 on the front surface of the flexible board 23. In the modification, the connection cables 39 are bonded to the electrode pads 21d likewise the first embodiment of the invention.

With the configuration described above, the external antenna 20A can achieve the same effect as the external antenna 20. Note that since the other configurations are the same as the first embodiment of the invention described above, a detailed explanation is not repeated here.

Modification 2

Figure 8:
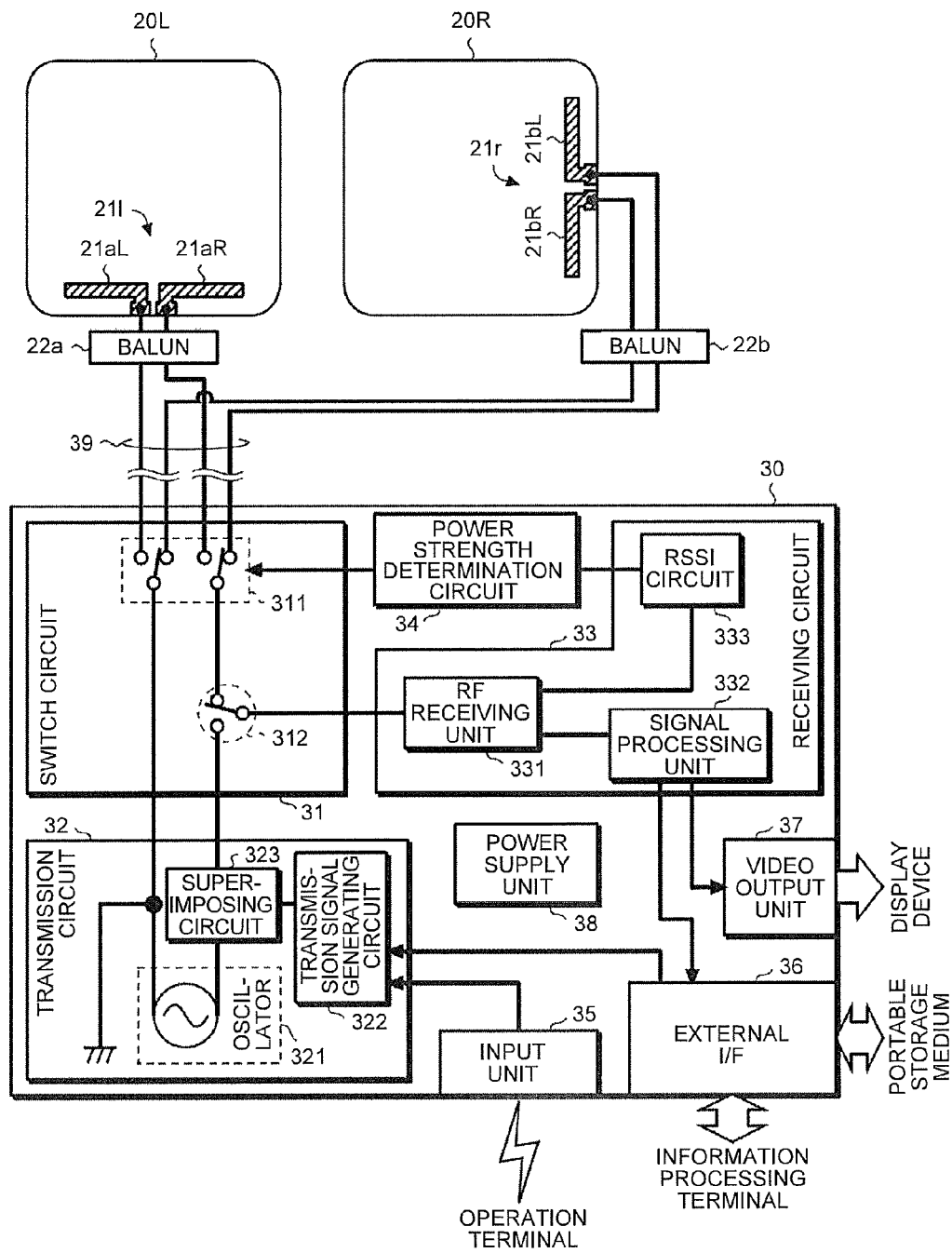
FIG. 8 is a schematic view showing a schematic configuration of an external antenna according to a modification 2 of the first embodiment of the invention.

Next, a modification 2 of the external antenna 20 according to the embodiment will be explained in detail with reference to the drawings. FIG. 8 is schematic view showing a schematic configuration of external antennas 20L and 20R according the modification. Note that, in FIG. 8, the external machine 30 connected to the external antennas 20L and 20R is also shown for the convenience of explanation.

As shown in FIG. 8, each of the external antennas 20L and 20R has one dipole antenna 21l or 21r. In the example, the external antenna 20L includes the dipole antenna 21l similar to the dipole antenna 21a of the external antenna 20, and the external antenna 20R includes the dipole antenna 21r similar to the dipole antenna 21b of the external antenna 20. Accordingly, a connection between the external antennas 20L and 20R and the external machine 30 is configured likewise the first embodiment of the invention.

With the configuration described above, the external antennas 20L and 20R can achieve the same effect as the external antenna 20. Further, since the two dipole antennas 21a and 21b can be greatly separated from each other as well as, when a radio wave is received, an influence, which is received by one dipole antenna from the other dipole antenna, can be reduced, a reception sensitivity (for example S/N ratio) can be prevented from being deteriorated by mutual interference. Note that since the other configurations are the same as the first embodiment of the invention described above, a detailed explanation is not repeated here.

Second Embodiment

Figure 9B:
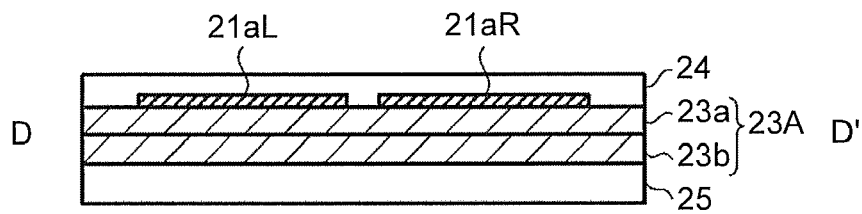
FIG. 9B is a D-D' sectional view of FIG. 9A.
Figure 9C:
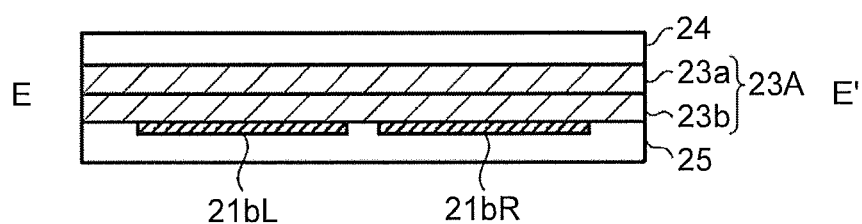
FIG. 9C is an E-E' sectional view of FIG. 9A.
Figure 9D:
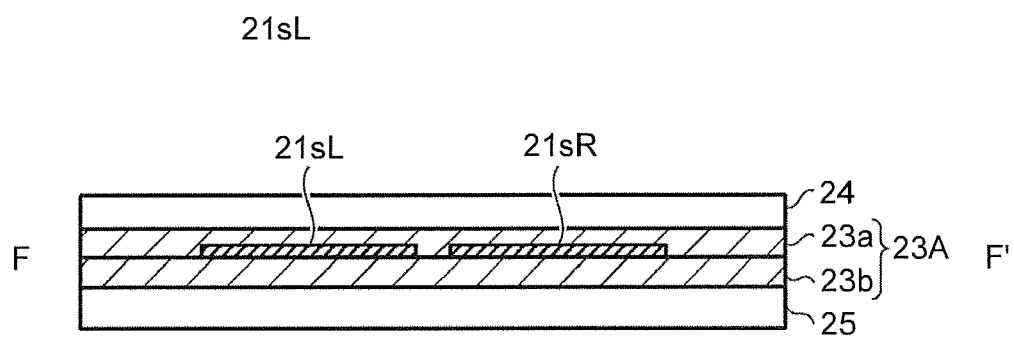
FIG. 9D is an F-F' sectional view of FIG. 9A.
Figure 10:
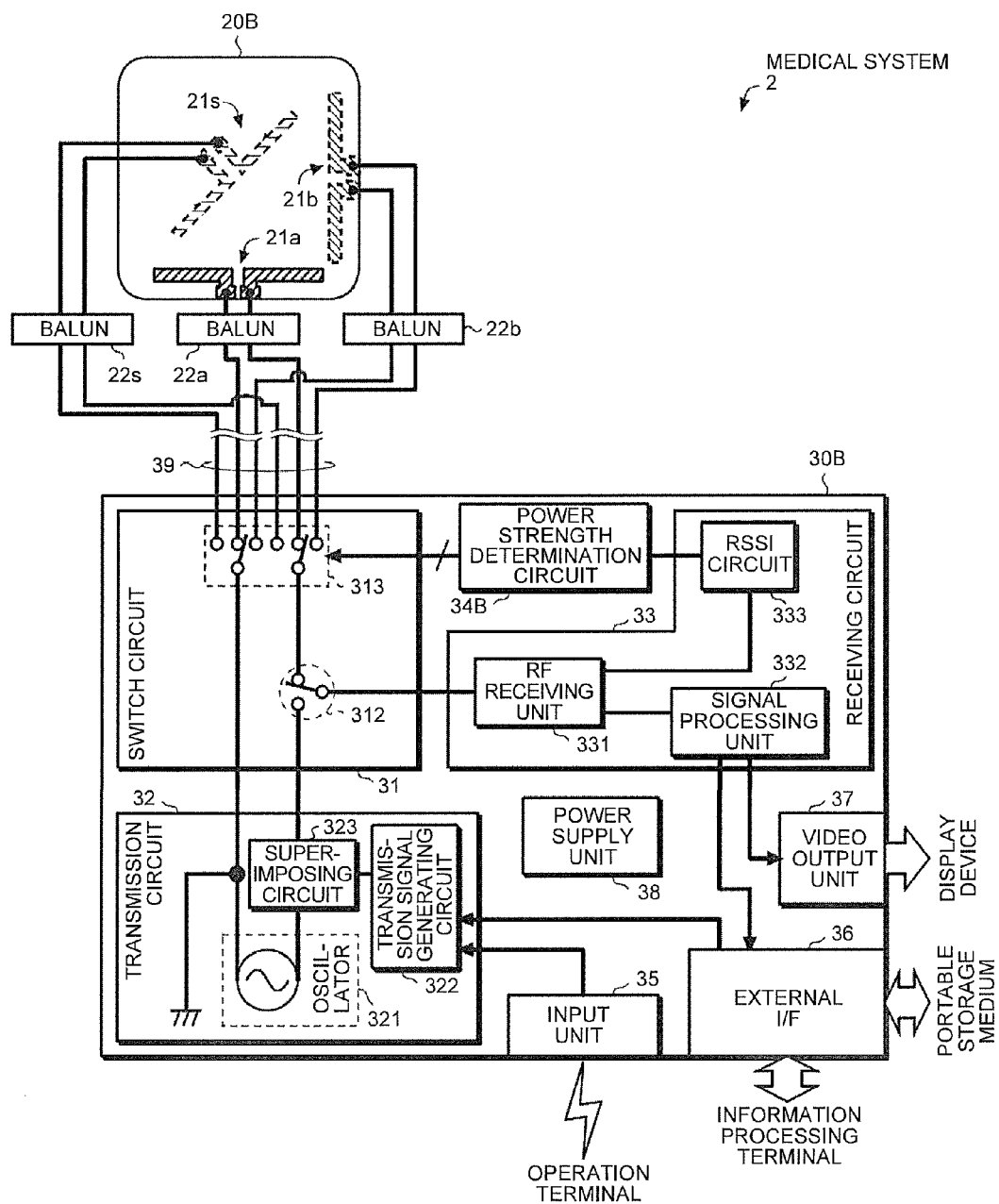
FIG. 10 is a schematic view showing a schematic configuration of a medical system according to the second embodiment of the invention.

Next, a medical system 2 according to a second embodiment of the invention will be explained in detail with reference to the drawings. FIG. 9A is an upper view showing a schematic configuration of an external antenna 20B according to the embodiment. Further, FIG. 9B is a D-D' sectional view of FIG. 9A, FIG. 9C is an E-E' sectional view of FIG. 9A, and FIG. 9D is an F-F' sectional view of FIG. 9A. Further, FIG. 10 is a schematic view showing a schematic configuration of the medical system 2 according to the embodiment. Note that, in FIG. 9A, the cover film 24 for protecting an antenna portion is omitted to clarify explanation.

As shown in FIG. 9A, the external antenna 20B includes a dipole antenna 21s disposed on an extending surface of a flexible board 23A obliquely to the two dipole antennas 21a and 21b of the external antenna 20 in addition to the dipole antennas 21a and 21b. The dipole antennas 21s include two elements 21sL and 21sR disposed symmetrically likewise the other dipole antennas 21a and 21b.

Further, as shown in FIGS. 9B to 9D, the flexible board 23A according to the embodiment has a layered structure composed of two flexible boards 23a and 23b. As shown in FIG. 9B, the dipole antenna 21a is formed on, for example, a front surface of an uppermost layer of the flexible board 23A. Further, as shown in FIG. 9C, the dipole antenna 21b is formed on, for example, a back surface of a lowermost layer of the flexible board 23A. Further, as shown in, for example, FIG. 9D, the dipole antenna 21s is formed on a layer between, for example, the flexible boards 23a and 23b.

Further, the respective elements 21sL and 21sR of the dipole antenna 21s formed on the intermediate layer of the flexible board 23A are electrically connected to the electrode pads 21d on the cover film 24 through via contacts 21c passing through, for example, the flexible board 23a and the cover film 24 on the flexible board 23A. In the embodiment, the connection cables 39 are bonded to the electrode pads 21d likewise the first embodiment of the invention.

In contrast, as shown in FIG. 10, in an external machine 30B according to the embodiment, the antenna changeover switch 311 composed of the two 2-way switches in the external machine 30 is replaced with an antenna changeover switch 313 composed of two 3-way switches. Further, a power strength determination circuit 34B for outputting a control signal for changeover controlling the antenna changeover switch 313 is configured to output a control signal capable of controlling the two 3-way switches. Note that the control signal can be, for example, a 4-value (for example, 2 bits) voltage signal.

With the configuration described above, according to the embodiment, even when the subject 100 takes a tilt position, since a horizontal polarized wave can be received by the dipole antenna 21s, a reception strength, which is more securely stabilized, can be realized in addition to an effect similar to the first embodiment of the invention. Note that since the other configurations are the same as the first embodiment of the invention described above, a detailed explanation is not repeated here.

Third Embodiment

Figure 11:
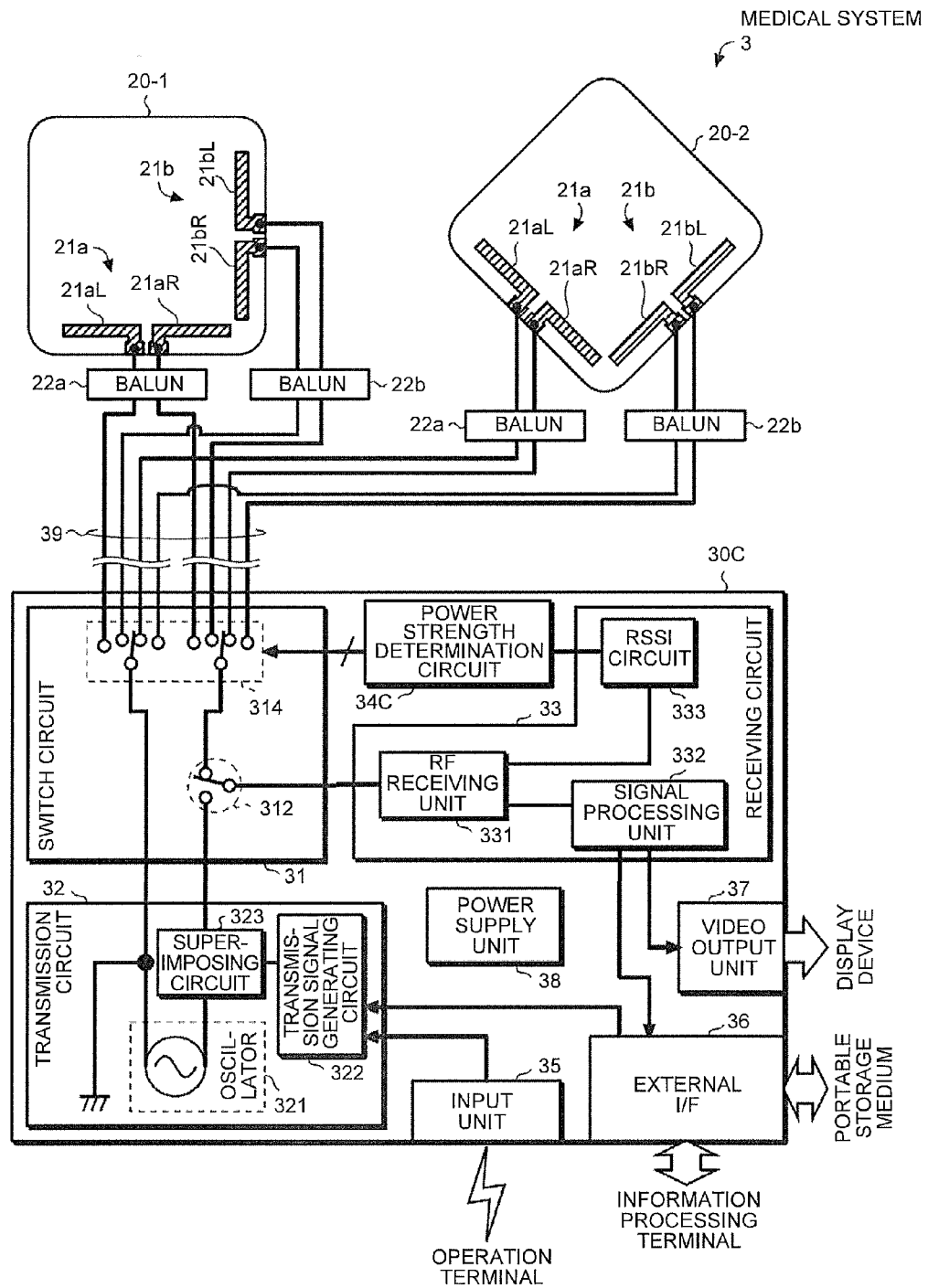
FIG. 11 is a schematic view showing a schematic configuration of a medical system according to a third embodiment of the invention.

Next, a medical system 3 according to a third embodiment of the invention will be explained in detail with reference to the drawings. FIG. 11 is a schematic view showing a schematic configuration of the medical system 3 according to the embodiment.

As shown in FIG. 11, in the medical system 3 according to the embodiment, two external antennas 20-1 and 20-2 are used. Further, the external machine 30 of the medical system 1 is replaced with an external machine 30C according to the configuration.

The individual external antennas 20-1 and 20-2 are the same as the external antenna 20 according to the first embodiment of the invention. However, in the embodiment, one external antenna 20-2 is bonded to the subject 100 so as to be oblique to the other the external antenna 20-1. That is, the dipole antenna 21a of the external antenna 20-1 tilts to the dipole antennas 21a and 21b of the external antenna 20-2, and the dipole antenna 21b of the external antenna 20-1 tilts to the dipole antennas 21a and 21b of the external antenna 20-2 likewise. With this configuration, even when the subject 100 takes a tilt position, since a horizontal polarized wave can be received by any dipole antenna 21a or 21b, a reception strength, which is more securely stabilized, can be realized.

In contrast, as shown in FIG. 11, in the external machine 30C according to the embodiment, the antenna changeover switch 311 composed of the two 2-way switches in the external machine 30 is replaced with an antenna changeover switch 314 composed of two 4-way switches. Further, a power strength determination circuit 34C for outputting a control signal for changeover controlling the antenna changeover switch 314 is configured to output a control signal capable of controlling the two 4-way switches. Note that the control signal can be configured as, for example, a quad (for example, 2 bits) voltage signal.

With the configuration described above, according to the embodiment, even when the subject 100 takes the tilt position, since a horizontal polarized wave can be received by the dipole antenna 21a or 21b disposed to the external antenna 20-2, a reception strength, which is more securely stabilized, can be realized in addition to an effect similar to the first embodiment of the invention. Note that since the other configurations are the same as the first embodiment of the invention described above, a detailed explanation is not repeated here.

Fourth Embodiment

Figure 12:
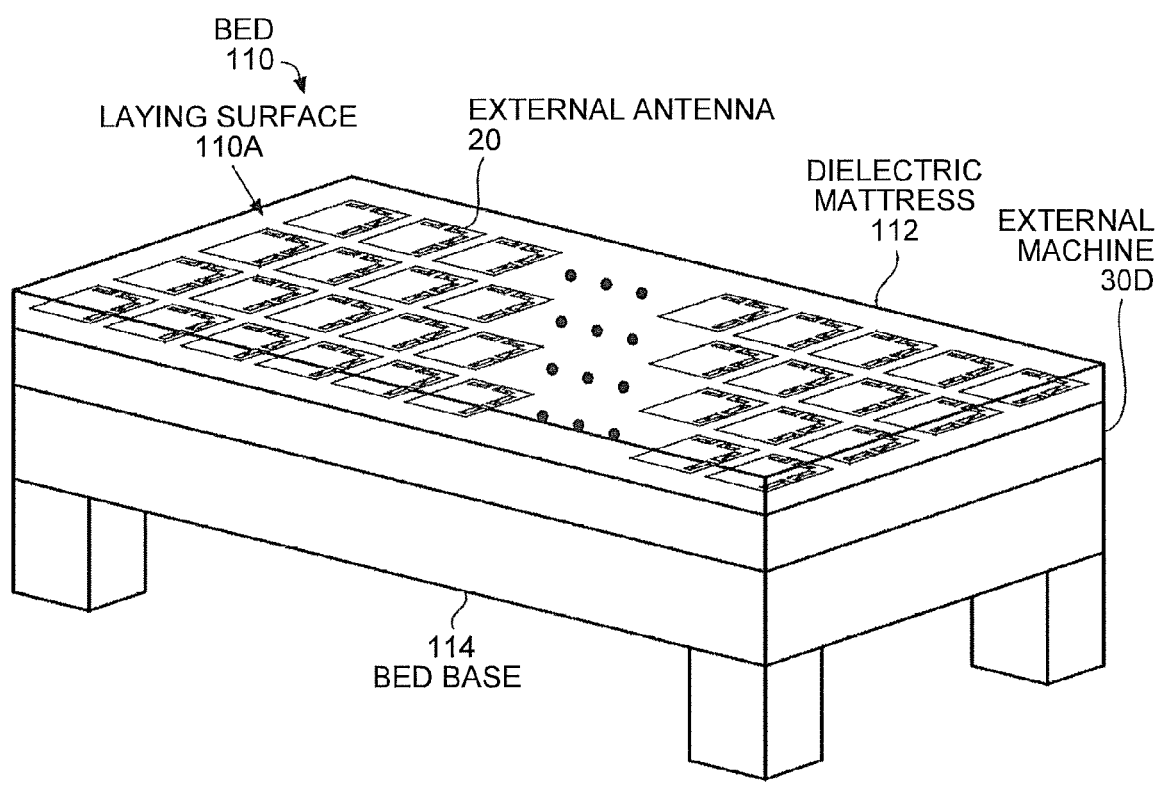
FIG. 12 is a perspective view showing schematic configurations of an external antenna and an external machine in a medical system according to a fourth embodiment of the invention.

Next, a medical system 4 according to a fourth embodiment of the invention will be explained in detail with reference to the drawings. FIG. 12 is a perspective view showing a schematic configuration of external antennas 20 and an external machine 30D in the medical system 4 according to the embodiment. Further, FIG. 13 is a schematic view showing a schematic configuration of the medical system 4 according to the embodiment.

As shown in FIG. 12, the embodiment has such a configuration that the plural external antennas 20 similar to the first embodiment of the invention are disposed in a two-dimensional array state along a horizontal surface under a laying surface 110A as an upper surface of a dielectric mattress 112 of a bed 110. Further, the external machine 30D is installed on, for example, a bed base 114 under the dielectric mattress 112 on which, for example, the plural external antennas 20 are disposed.

The dielectric mattress 112 is preferably formed using a material having a high dielectric constant as large as a dielectric constant of the subject 100. With this configuration, since a dielectric constant between the subject 100 and the external antennas 20 can be set to an approximately continuous value, a reflection of a radio wave generated between the subject 100 and the dielectric mattress 112 can be suppressed and thus a stronger reception strength can be obtained.

Figure 13:
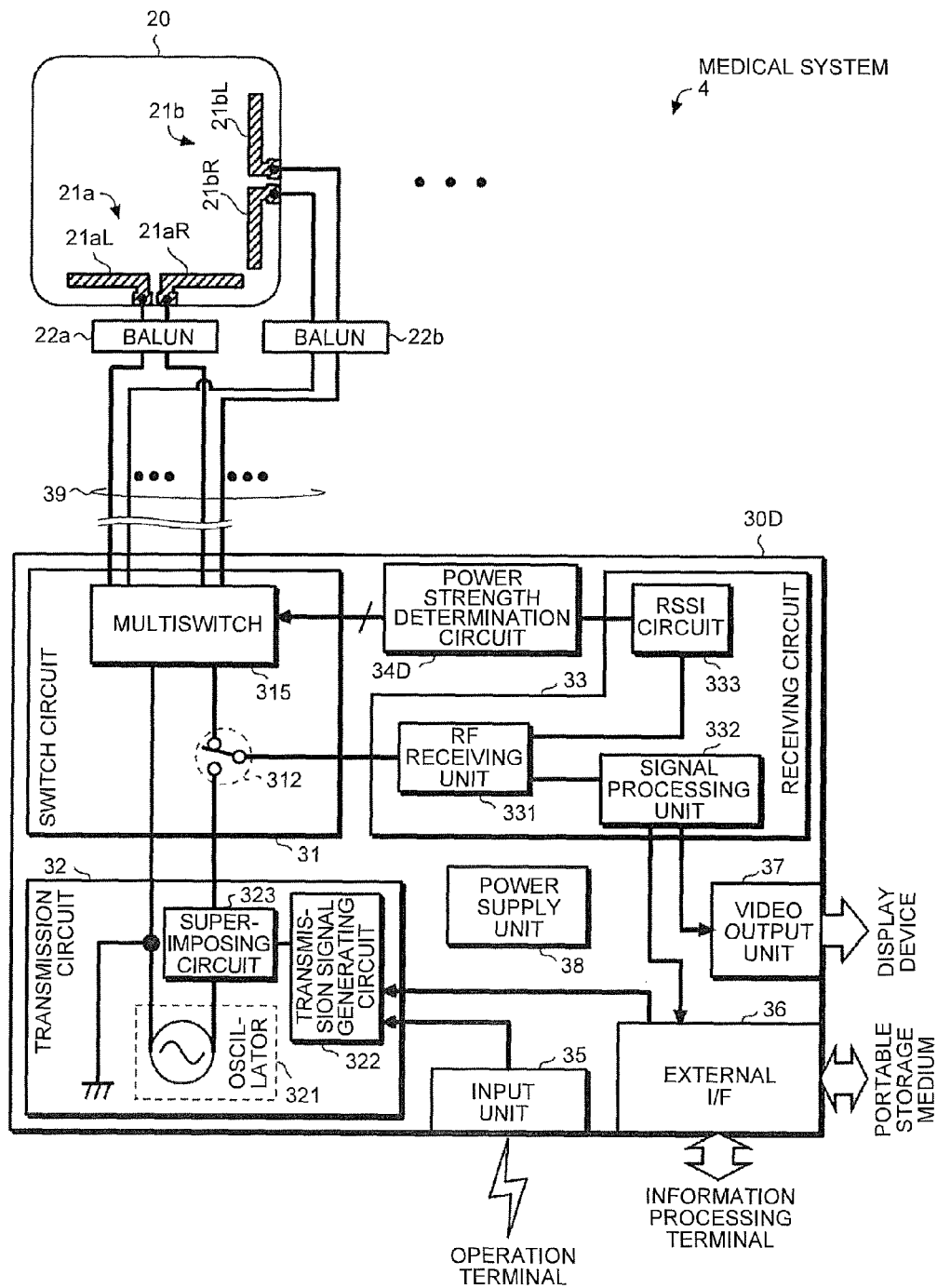
FIG. 13 is a schematic view showing a schematic configuration of the medical system according to the fourth embodiment of the invention.

Further, as shown in FIG. 13, the respective external antennas 20 and the external machine 30D in the medical system 4 are connected using the connection cables 39 to which, for example, the baluns 22a and 22b are disposed likewise the connection configuration of the external antenna 20 and the external machine 30 shown in FIG. 5. However, a multiswitch 315, which can execute change-over according to the external antennas 20 and the number of dipole antennas disposed to the external antennas 20, is used to change over a connecting relation of the external antennas 20 and inside of the external machine 30D.

Further, the external machine 30D is configured so that it can be connected to the operation terminal 60 through a wireless line or a wired line and connected to the information processing terminal 50 through the communication cable 59, can connect an external storage medium such as the portable storage medium 40 thereto, and can be connected to a display device through a not shown monitor cable likewise the external machine 30 shown in FIG. 2.

In the medical system 4, when the capsule type medical apparatus 10 introduced into the subject 100 on the bed 110 executes a communication with the external machine 30D, the external machine 30D causes a power strength determination circuit 34D to determine that when any dipole antenna (21a or 21b) of any of the external antennas 20 is used, a highest reception strength can be obtained by detecting reception intensities obtained by the respective dipole antennas (21a, 21b) by scanning the respective dipole antennas 21a and 21b of the plural external antennas 20 by controlling the multiswitch 315 and thereafter comparing the reception intensities and executes the communication in a state that the external machine 30D causes the power strength determination circuit 34D to select the dipole antenna (21a or 21b) of the external antenna 20 by which the highest reception strength can be obtained. With this operation, the communication can be executed using the dipole antenna 21a or 21b of the external antenna 20 having the most excellent reception strength.

Note that, since the other configurations and operations as well as an effect obtained thereby are the same as the first embodiment described above, a detailed explanation is not repeated here. Further, although the external antenna 20 according to the first embodiment of the invention is used in the embodiment, the invention is not limited thereto, and it is needless to say that the external antennas according to the modifications thereof and the other embodiments can also be used.

Fifth Embodiment

First, a configuration and an operation of a medical system 5 according to a fifth embodiment of the invention will be explained in detail with reference to the drawings. Note that the embodiment will be explained exemplifying a case that an inner wall image of the stomach 102 is obtained using the capsule type medical apparatus 10 which floats on a liquid 104 stored in the stomach 102. However, the invention is not limited to the case and can also be applied to a capsule type medical apparatus for obtaining some kind of information in the subject 100 while moving from an esophagus to an anus. Further, in-subject information obtained by the capsule type medical apparatus 10 is not limited to a captured image and may be various information such as an in vivo pH value, a cell tissue, a blood, a body fluid, and the like. Further, a body part in which the liquid 104 is stored is not limited to the stomach 102 and may be various organs, for example, a small intestine, a large intestine, and the like. Further, liquids, for example, normal saline, water, and the like, which do not adversely affect the subject 100 and the capsule type medical apparatus 10, are preferably used as the liquid 104. Note that the liquid 104 is preferably transparent. As a result, it can be avoided that a captured image is made unclear by the liquid 104 when an in-subject image is obtained as, for example, in-subject information.

Figure 14:
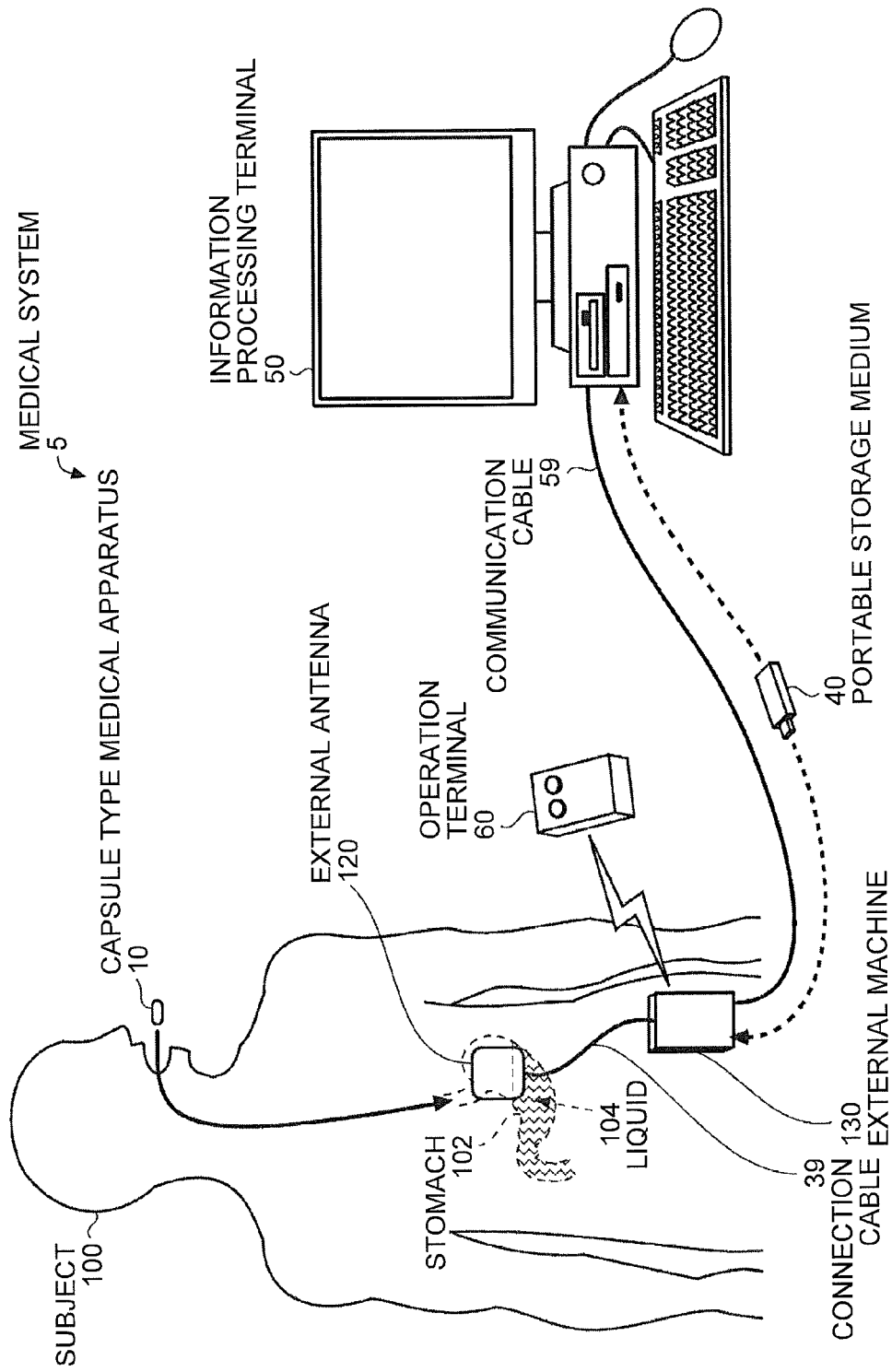
FIG. 14 is a schematic view showing a schematic configuration of a medical system according to the first embodiment of the invention.

FIG. 14 is a schematic view showing a schematic configuration of the medical system 5 according to the embodiment. As shown in FIG. 14, the medical system 5 includes the capsule type medical apparatus 10, which floats on the liquid 104 introduced into the subject 100, for example, orally and stored in the stomach 102, and an external machine 130 for transmitting and receiving image data, a control command, and the like between it and the capsule type medical apparatus 10 by executing a wireless communication with the capsule type medical apparatus 10. An external antenna 120 is connected to the external machine 130 through connection cables 139, and the external machine 130 and the capsule type medical apparatus 10 execute a wireless communication using the external antenna 120. Note that although the external machine and the external antenna are explained separately in the following explanation, the invention is not limited to the configuration and the external antenna and the external machine may be configured as one external device.

Further, the external machine 130 may be configured so that, for example, it can execute a wireless/wired communication with the operation terminal 60 to which the operator inputs various kinds of operations such as an imaging instruction and the like. Further, the external machine 130 may be configured so that it can be connected to the information processing terminal 50 such as a personal computer, a workstation, and the like through the communication cable 59, for example, a USB (Universal Serial Bus) cable and a LAN (Local Area Network) cable. Further, the external machine 130 may be configured so that an external storage medium such as the portable storage medium 40 and the like can be attached thereto. Further, the external machine 130 may be configured so that a display device such as a liquid crystal display and the like can be connected thereto through, for example, a not shown monitor cable. Note that the external machine 130 itself may be provided with an input unit for inputting various kinds of operations, a storage unit such as an EEPROM (Electrically Erasable Programmable Read Only Memory) and the like, and a display unit such as a liquid crystal display and the like.

Capsule Type Medical Apparatus

Figure 15:
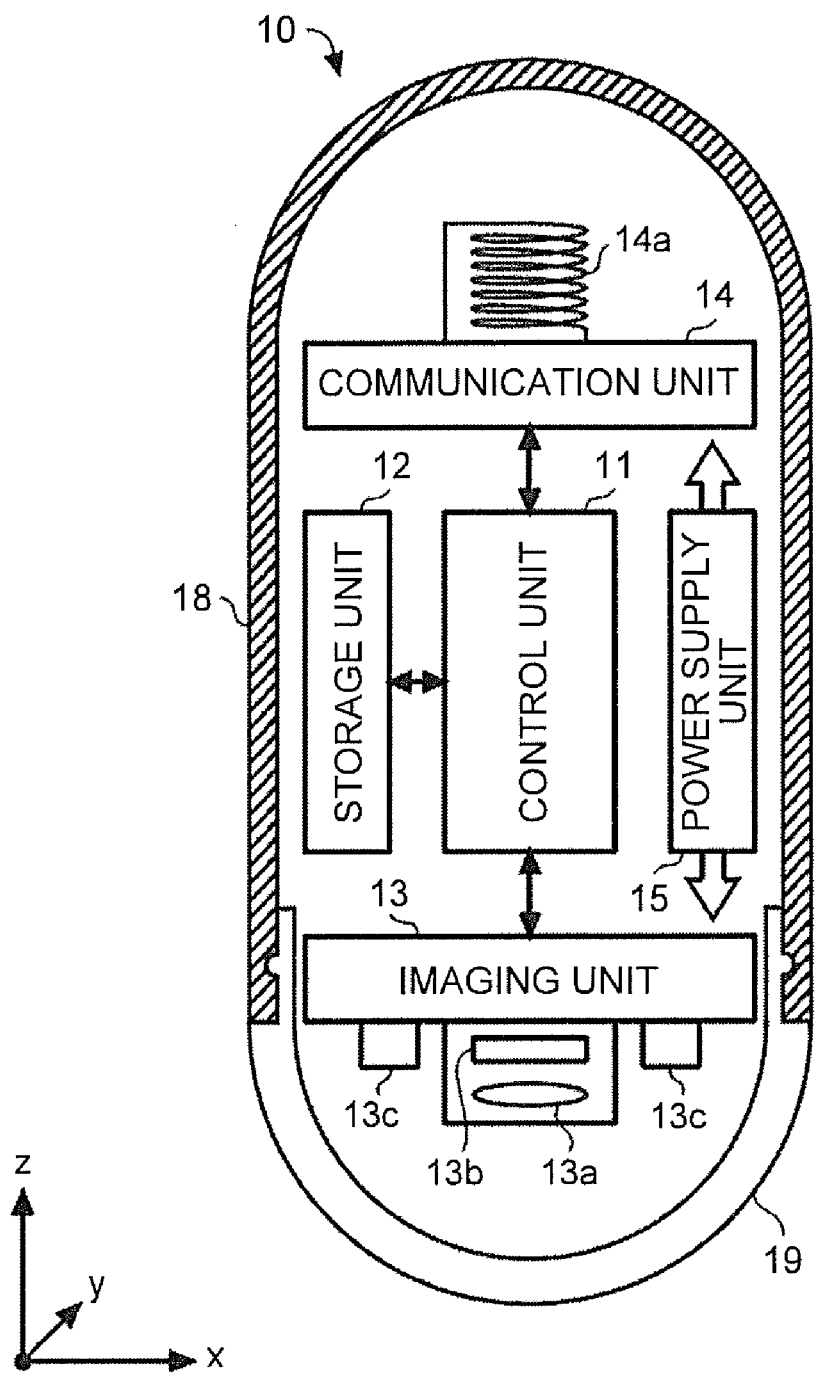
FIG. 15 is a schematic view showing a schematic configuration of the capsule type medical apparatus according to the first embodiment of the invention.

Here, an example of the capsule type medical apparatus 10 according to the embodiment will be explained in detail with reference to the drawings. FIG. 15 is a schematic view showing a schematic configuration of the capsule type medical apparatus 10 according to the embodiment. As shown in FIG. 15, the capsule type medical apparatus 10 includes the imaging unit 13 for obtaining an image in, for example, the subject 100, the communication unit 14 for executing a wireless communication with the external machine 130, the control unit 11 for controlling respective portions (units) in the capsule type medical apparatus 10 such as the imaging unit 13, the communication unit 14, and the like, the storage unit 12 for storing image data of an in-subject image obtained by the imaging unit 13, various kinds of data such as a control command and the like received through the communication unit 14, various kinds of programs and the like executed by the control unit 11 to control the respective portions in the capsule type medical apparatus 10, and the power supply unit 15 for supplying power to the respective portions in the capsule type medical apparatus 10.

The control unit 11 realizes various kinds of operations such as an imaging operation and a transmission/receiving operation in the respective portions by controlling/driving the respective portions (units) in the capsule type medical apparatus 10 based on various kinds of control programs read from, for example, the storage unit 12 and on the control command and the like received from the external machine 130 through the communication unit 14. The control unit 11 can be configured using an information processing device, for example, a CPU (Central Processing Unit), an MPU (Microprocessor), and the like.

The storage unit 12 stores various kinds of control programs appropriately executed by the control unit 11, image data obtained by the imaging unit 13, various kinds of data received through the communication unit 14, other configuration information, and the like. The storage unit 12 can be configured using, for example, a RAM (Random Access Memory) and the like. Further, the storage unit 12 may include a ROM (Read Only Memory) for storing the various kinds of control programs described above. Further, the storage unit 12 may store image data received from the capsule type medical apparatus 10 in addition to the various kinds of data, the other configuration information, and the like.

The imaging unit 13 has such a configuration that it is mounted on a circuit board on which, for example, the imaging unit 13a for obtaining an image in the subject 100 as image data, the optical lens 13b disposed on a light receiving surface side of the imaging unit 13a, and at least one illumination 13c for illuminating inside of the subject 100 when an image is captured have a predetermined drive/control circuit, wirings, and the like. The imaging unit 13 appropriately obtains an in-subject image (inner wall image of the stomach 102) as image data by operating under a control from the control unit 11. The obtained image data is recorded in the storage unit 12 through, for example, the control unit 11 or sent to the external machine 130 from the communication unit 14. Note that a CCD (Charge Coupled Device) camera, a CMOS (Complementary Metal Oxide Semiconductor) camera, and the like, for example, can be used as the imaging unit 13a. Further, an LED (Light Emitting Diode), for example, can be used as the illumination 13c. Note that the capsule type medical apparatus 10 may include plural imaging units 13.

The communication unit 14 for realizing a communication means (first communication unit) using the antenna 14a has such a configuration that the antenna 14a is mounted on a circuit board having a predetermined transmission/receiving circuit, wirings, and the like, appropriately transmits the image data obtained by the imaging unit 13 or the image data stored in the storage unit 12 to the external machine 130 by operating under the control from the control unit 11, and further receives the various kinds of data such as a control command and the like transmitted from the external machine 130 and inputs the various kinds of data to the control unit 11. Note that, in the embodiment, a coil antenna (also called a loop antenna) for outputting a radio wave, in which at least one of a vertical polarized wave and a horizontal polarized wave has directionality, is used as the antenna 14a (first antenna). This is because the coil antenna has a large gain in a small antenna. However, the invention is not limited to the coil antenna and, for example, various antennas can be used.

Further, the respective portions described above are accommodated in a capsule type vessel (casing) composed of an approximately cylindrical or semi-oval spherical main vessel (first casing) 18 having one end formed in a hemispherical dome shape and the other end opened and a hemispherical sub vessel (second casing) 19 for sealing inside of the main vessel 18 by being engaged with the opening of the main vessel 18. The capsule type vessels (18, 19) have such a degree of size that, for example, the subject 100 can swallow the vessels. Further, in the embodiment, at least the sub vessel 19 is formed of a transparent material as well as the imaging unit 13 described above is disposed to the sub vessel 19 side facing an external direction. With this configuration, the imaging unit 13 can capture the inner wall of the stomach 102 through the transparent sub vessel 19. Note that the main vessel 18 may be formed in an approximately cylindrical shape having both ends opened, and the inside of the main vessel 18 may be sealed by engaging the sub vessels 19 formed of the transparent material with the two openings, respectively. In this case, the capsule type medical apparatus 10 can mount the imaging units 13 to both of the ends, respectively. Note that the respective imaging units 13 are disposed facing the external directions.

In addition to the configurations described above, the capsule type medical apparatus 10 according to the embodiment is configured such that an overall specific gravity becomes smaller than a specific gravity of the liquid 104. As a result, the capsule type medical apparatus 10 can be caused to float on a liquid surface of the liquid 104 stored in the stomach 102. However, the specific gravity of the capsule type medical apparatus 10 is not necessarily smaller than the specific gravity of the liquid 104.

Further, a center of gravity of the capsule type medical apparatus 10 is offset from centers of the overall capsule type vessels (18, 19) so that the capsule type medical apparatus 10 keeps its posture (a posture to, for example, the ground surface) constant regardless of a posture of the subject 100 in the stomach 102 of the subject 100. In the embodiment, when the ground surface is, for example, an xy plane in FIG. 15, the center of gravity of the capsule type medical apparatus 10 is offset so that a longitudinal direction of the capsule type medical apparatus 10 floating on the liquid 104 keeps, for example, a z-direction as well as the sub vessel 19, which forms an imaging window, is positioned on a lower side.

The offset of the center of gravity can be realized by disposing a member having a large specific gravity on the sub vessel 19 side in, for example, an internal configuration. Since, for example, a button battery and the like used as the power supply unit 15 have a large specific gravity in comparison with the other configurations, when the button battery and the like are disposed on the sub vessel 19 side, the center of gravity of the capsule type medical apparatus 10 can be offset to the sub vessel 19 side. Note that it is needless to say that the center of gravity can be offset by various configurations by, for example, offsetting an overall internal configuration to the sub vessel 19 side and the like.

As described above, a direction of the antenna 14a of the communication unit 14 can be restricted by configuring the capsule type medical apparatus 10 so that the posture of the capsule type medical apparatus 10 floating on the liquid 104 is kept in a predetermined direction. Thus, in the embodiment, as shown in, for example, FIG. 15, the antenna 14a is fixed in the capsule type medical apparatus 10 (for example, on the circuit board of the communication unit 14) so that a winding axis of the antenna 14a is vertical (z-direction) to the liquid surface (the ground surface, that is, the xy plane). With this configuration, since the capsule type medical apparatus 10 is configured to receive the horizontal polarized wave using the external antenna 120 to be described later even when the subject 100 takes any posture, it can be prevented that a reception efficiency is lowered by a body position of the subject 100. Further, since the horizontal polarized wave has such characteristics that a reflection loss is small on a boundary surface between a liquid (for example, the liquid 104) and a gas (for example, a gas in the stomach 102), a radio wave from the capsule type medical apparatus 10 can be received more efficiently by configuring the horizontal polarized wave so that it can be received regardless of the body position of the subject 100. Note that a relation among the direction of the antenna 14a, the posture of the subject 100, and the external antenna 120 will be described later.

Further, it is sufficient that the specific gravity of the capsule type medical apparatus 10 has such a degree of specific gravity that at least a part of the capsule type medical apparatus 10 projects on the liquid surface of the liquid 104.

External Antenna

Figure 16A:
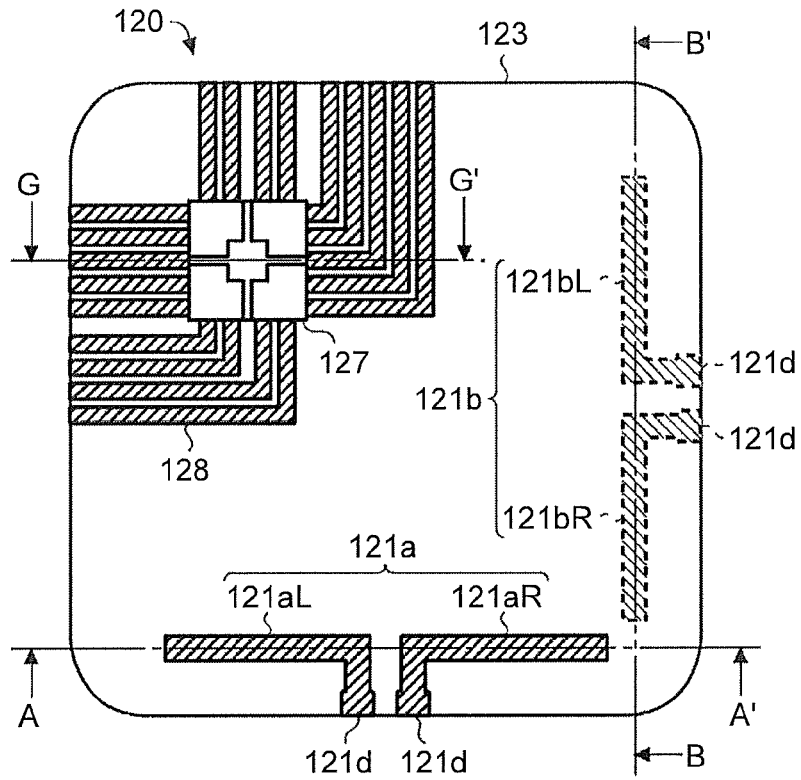
FIG. 16A is an upper view showing a schematic configuration of the external antenna according to the first embodiment of the invention.
Figure 16B:
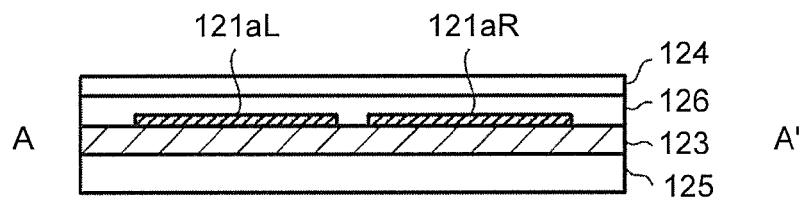
FIG. 16B is an A-A' sectional view of FIG. 16A.
Figure 16C:
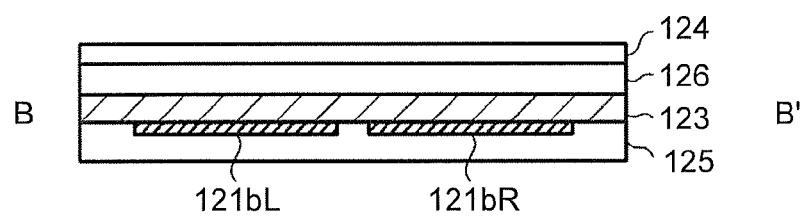
FIG. 16C is a B-B' sectional view of FIG. 16A.
Figure 16D:
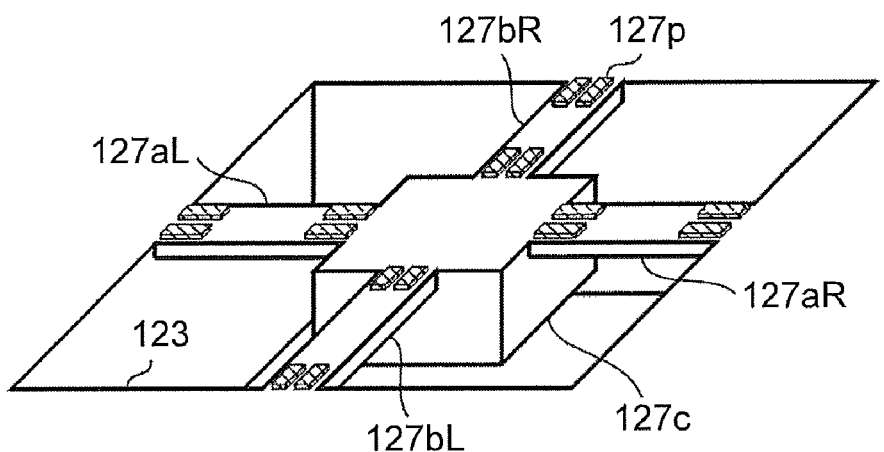
FIG. 16D is a perspective view of a schematic configuration of an acceleration sensor 27 disposed to an external antenna 20.
Figure 16E:
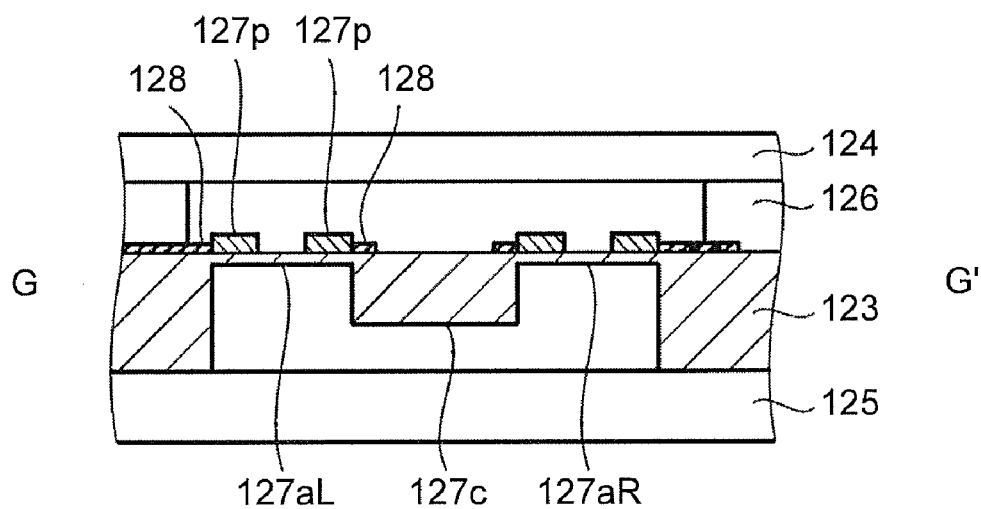
FIG. 16E is a G-G' sectional view of FIG. 16A.

Next, an example of the external antenna 120 according to the embodiment will be explained in detail with reference to the drawings. FIGS. 16A to 16E are schematic views showing a schematic configuration of the external antenna 120 according to the embodiment. Note that FIG. 16A is an upper view of the external antenna 120, FIG. 16B is an A-A' sectional view of FIG. 16A, and FIG. 16C is a B-B' sectional view of FIG. 16A. Further, FIG. 16D is a perspective view showing a schematic configuration of an acceleration sensor 27 disposed to the external antenna 120, and FIG. 16E is a sectional view G-G' of FIG. 16A. Further, in FIG. 16A, a cover film 124 for protecting an antenna portion and a spacer film 26 for securing a movable region of the spindle portion 27c of the acceleration sensor 27 to be described later are omitted to clarify explanation.

As shown in FIG. 16A, the external antenna 120 has a configuration in which two dipole antennas 121a and 121b are formed on front/back surfaces of an approximately square flexible board 123. However, the invention is not limited to the dipole antennas and can use various antennas, for example, loop antennas, micro strip antennas (also called patch antennas), and the like.

The dipole antenna 121a includes two elements 121aL and 121aR disposed symmetrically. In contrast, the dipole antenna 121b includes two elements 121bL and 121bR disposed symmetrically likewise. Electrode pads 121d are disposed to the respective elements 121aL, 121aR, 121bL, and 121bR to electrically guide them to an end of the flexible board 123.

Further, the dipole antenna 121a (second antenna) and the dipole antenna 121b (third antenna) are disposed so that extending directions of the respective elements of them are orthogonal to each other. With this configuration, in the embodiment, since the external antenna 120 is configured so that it has plural different polarized wave surfaces, even when the external antenna 120 is positioned in a horizontal direction to the capsule type medical apparatus 10, a horizontal polarized wave in a radio wave output from the antenna 14a of the capsule type medical apparatus 10 can be received using any of the dipole antennas (21a or 21b). As a result, the radio wave from the capsule type medical apparatus 10 can be efficiently received regardless of a body position of the subject 100.

As shown in FIG. 16B, the dipole antenna 121a is formed on, for example, one of main surfaces (which is a front surface) of the flexible board 123. In contrast, as shown in FIG. 16C, the dipole antenna 121b is formed on, for example, the other main surface (which is a back surface) of the flexible board 123. However, the dipole antennas 121a, 121b are not limited to the above configurations, and both of them may be formed on the same surface and on the same layer of the flexible board 123.

Further, as shown in FIG. 16B or in FIG. 16C, the front surface of the flexible board 123 on which the dipole antennas 121a and 121b are formed is covered with the cover film 124 for protecting the dipole antenna 121a formed on the flexible board 123 across the spacer film 26 for securing the movable region of the spindle portion 27c of the acceleration sensor 27. In contrast, an adhesive film 125 is formed on the back surface of the flexible board 123 to attach the external antenna 120 to the subject 100. The adhesive film 125 also plays a role for protecting the dipole antenna 121b formed on the back surface of the flexible board 123. However, the external antenna 120 is not limited to the above configuration and may be configured to be attached to, for example, clothing such as a jacket and the like. In this case, when the external antenna 120 is detachably attached to the clothing, various configurations such as a magic tape (registered trademark) and the like can be used.

Here, a film like substrate, which is composed of a material having a plastic property and further having the same dielectric constant as a dielectric constant of the subject 100, is preferably used as the flexible board 123. Likewise, a material having a plastic property and further having the same dielectric constant as the dielectric constant of the subject 100 is preferably used as the adhesive film 125 disposed between the dipole antennas 121a and 121b and the capsule type medical apparatus 10. However, "the same dielectric constant" referred to in the invention may not necessarily be the same and may be a dielectric constant capable of reducing a reflection of a radio wave from the antenna 14a in such a degree that "the same dielectric constant" can be regarded as large as the dielectric constant of the subject 100. With this configuration, since the flexible board 123 can be caused to come into intimate contact with the subject 100 using the adhesive film 125 as well as the reflection of the radio wave by the flexible board 123 and/or the adhesive film 125 can be suppressed, a stronger reception strength can be obtained. Further, when the external antenna 120 is attached to the clothing such as the jacket and the like, the clothing is preferably formed of a material having the same dielectric constant as the dielectric constant of the subject 100.

Note that, in the embodiment, although a case that the dipole antennas 121a and 121b, which are orthogonal to each other, are formed on the front/back surfaces of the single layer flexible board 123 is exemplified, the invention is not limited thereto, and the dipole antennas 121a and 121b may be formed on any of the same or different layers of a flexible board having, for example, a layered structure.

Further, the external antenna 120 includes the acceleration sensor (also called a gravity sensor) 27 for detecting a tilt of the external antenna 120 to the ground surface (that is, a posture of the subject 100). As shown in FIGS. 16D and 16E, the acceleration sensor 27 has the spindle portion 27c and beam portions 27aL, 27aR, 27bL and 27bR made to the flexible board 123 using, for example, an MEMS (Micro Electro Mechanical System) processing technology.

As shown in FIG. 16D, the spindle portion 27c is supported from four directions using the beam portions 27aL, 27aR, 27bL and 27bR. The respective beam portions 27aL, 27aR, 27bL and 27bR are formed fragile in such a degree that they are flexed by a weight of the spindle portion 27c. Further, piezo resistor elements 27p whose resistance value is changed by the deformation thereof caused by external stress are bonded to root portions of the respective beam portions 27aL, 27aR, 27bL and 27bR to the flexible board 123 and to a root portion thereof to the spindle portion 27c. That is, the acceleration sensor 27 according to the embodiment is a piezo type 3-axis acceleration sensor. Accordingly, in the embodiment, the tilt of the external antenna 120 to the ground surface can be detected by detecting a resistance ratio of the piezo resistor elements 27p due to the flexure of the respective beam portions 27aL, 27aR, 27bL and 27bR.

The piezo resistor elements 27p bonded to the respective beam portions 27aL, 27aR, 27bL and 27bR are connected by wirings 28 formed on the front surface of the flexible board 123 as well as electrically drawn out to an end of the flexible board 123. The connection cables 139 are bonded to the wirings 28 drawn out to the end of the flexible board 123. With this configuration, the acceleration sensor 27 is connected to the external machine 130.

Note that the invention is not limited to the piezo type 3-axis acceleration sensor described above, and various kinds of acceleration sensors (gravity sensors), for example, a capacitive type 3-axis acceleration sensor using an MEMS structure, and the like can be used. Note that the respective piezo resistor elements 27p of the acceleration sensor 27 are connected to a tilt angle detection circuit 134 of the external machine 130 through the connection cables 139 for connecting the external antenna 120 to the external machine 130. Detection of a gravity direction (or a tilt direction of the external antenna 120) by the tilt angle detection circuit 134 will be described later.

External Machine

Figure 17:
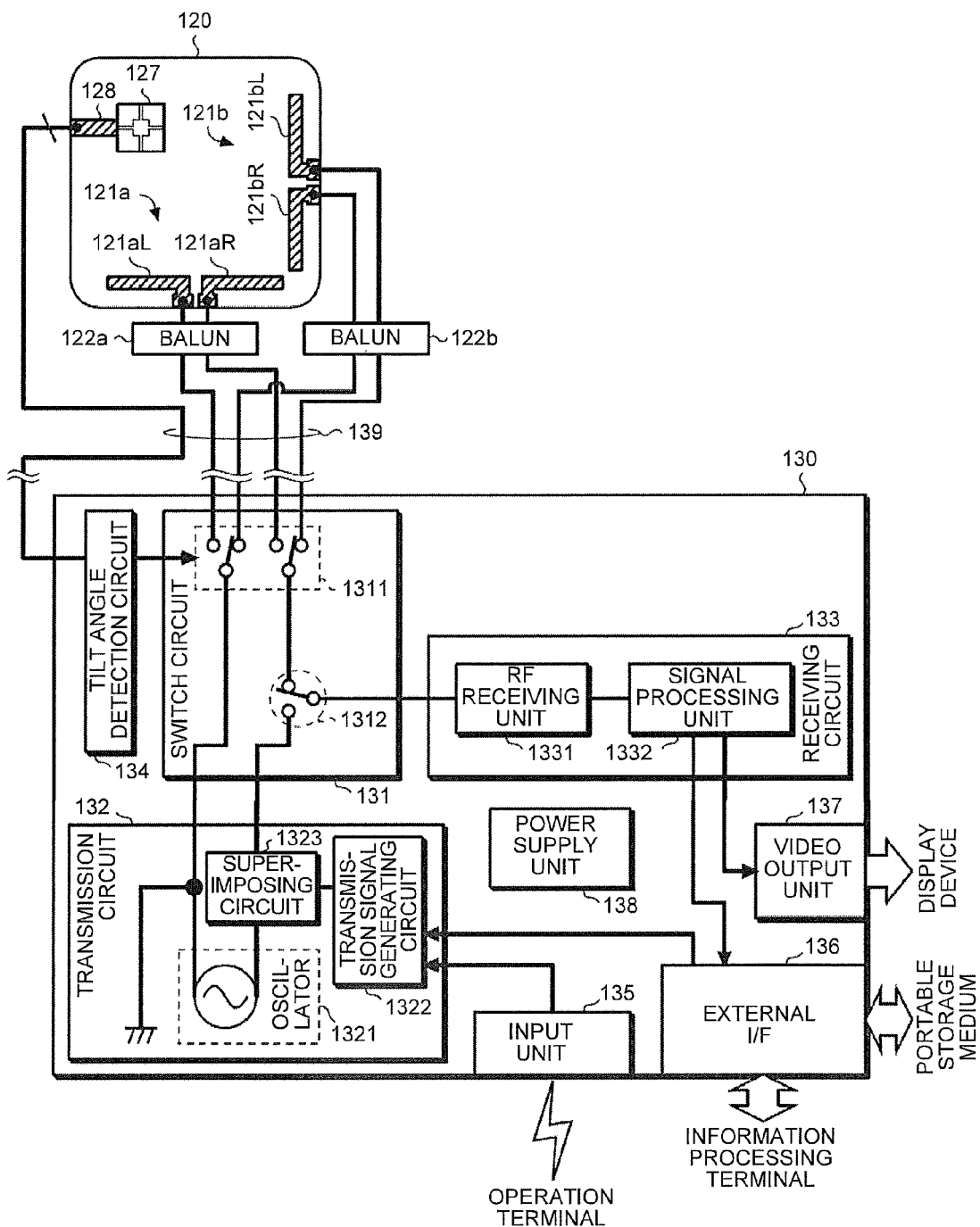
FIG. 17 is a schematic view showing a schematic configuration of the external machine according to the first embodiment of the invention.

Next, an example of the external machine 130 according to the embodiment will be explained in detail with reference to the drawings. FIG. 17 is a schematic view showing a schematic configuration of the external machine 130 according to the embodiment. As shown in FIG. 17, the external machine 130 includes a switch circuit 131 for switching an antenna configuration and a transmission/receiving of the external antenna 120, a transmission circuit 132 for creating a transmission signal in which various kinds of data such as an input control command and the like are superimposed to a predetermined transmission frequency, an input unit 135 for inputting the various kinds of data such as the control command and the like input from the operation terminal 60 (refer to FIG. 14) to the transmission circuit 132, a receiving circuit 133 for reproducing a reception signal input through the external antenna 120 to a data signal, the tilt angle detection circuit 134 for detecting a tilt direction of the external antenna 120 based on a resistance value detected by the acceleration sensor 27 of the external antenna 120, a video output unit 137 for converting image data of the data signal reproduced by the receiving circuit 133 to video data to be displayed on an external display device and outputting the video data, an external interface (I/F) 136 for controlling a connection to the information processing terminal 50 (refer to FIG. 14) and the portable storage medium 40 (refer to FIG. 14), and a power supply unit 138 for supplying power to the respective portions described above.

In the above configuration, the switch circuit 131 includes an antenna changeover switch 1311 for changing over an antenna to be used as any of the two dipole antennas 121a and 121b of the external antenna 120 and a transmission/receiving changeover switch 1312 for changing over a connection destination in the external machine 130 of the external antenna 120.

The antenna changeover switch 1311 is composed of at least two 2-way switches configured using, for example, plural switching transistors, and change-over terminals of the respective 2-way switches are appropriately connected to the electrode pads 121d of the respective elements (21aL or 21bL, and, 121aR or 21bR) of the dipole antennas 121a and 121b through the connection cables 139 and baluns 122a, 122b. The antenna changeover switch 1311 changes over an antenna to be used as any of the two dipole antennas 121a and 121b disposed to the external antenna 120 based on a control signal output from the tilt angle detection circuit 134 to be described later. With this operation, any of plural polarized wave surfaces of the external antenna 120 can be selected. More specifically, the antenna changeover switch 1311 functions as a selection means for selecting any of the plural polarized wave surfaces of the external antenna 120. Further, the balun 122a and the balun 122b, which are equilibrium/non-equilibrium conversion circuits for converting electric signals in equilibrium and non-equilibrium states, are disposed on the connection cables 139 for connecting the respective dipole antennas 121a and 121b and the antenna changeover switch 1311.

The transmission/receiving changeover switch 1312 is a 2-way switch configured using, for example, plural switching transistors and switches a connection destination of the external antenna 120 to any of the transmission circuit 132 and the receiving circuit 133 in transmission and in reception. The transmission/receiving changeover switch 1312 can be configured so that it is controlled by, for example, the tilt angle detection circuit 134 to be described later, a not shown control unit, and the like.

The transmission circuit 132 includes an oscillator 1321 for oscillating in a predetermined transmission frequency based on a not shown reference voltage, a transmission signal generating circuit 1322 for creating a transmission signal from the various kinds of data such as the control command and the like input from the input unit 135 and the external I/F 136 or the not shown control unit, and a superimposing circuit 1323 for superimposing the transmission signal created by the transmission signal generating circuit 1322 to a transmission frequency signal output from the oscillator 1321. Accordingly, in transmission, the transmission signal is superimposed in the superimposing circuit 1323 to the oscillation frequency signal output from the oscillator 1321, and thereafter, the transmission frequency signal, to which the transmission signal is superimposed, is input to the external antenna 120 through the switch circuit 131 and transmitted to the external capsule type medical apparatus 10 as a radio wave signal from any of the dipole antenna 121a or 21b of the external antenna 120.

The receiving circuit 133 includes an RF receiving unit 1331 for reproducing data sent from the capsule type medical apparatus 10 by subjecting a frequency signal input from the external antenna 120 through the switch circuit 131 to filtering, down convert, demodulation, decode, and the like and for outputting reception data and a signal processing unit 1332 for executing a predetermined processing using the reception data output from the RF receiving unit 1331.

As described above, at least one of the transmission circuit 132 and the receiving circuit 133 functions as a communication means (second communication unit) for executing a communication with the capsule type medical apparatus 10 through the dipole antenna (21a or 21b) selected by the antenna changeover switch 1311.

Note that after the reception data, which is reproduced by the RF receiving unit 1331, is subjected to a predetermined processing such as pixel interpolation and the like in, for example, the signal processing unit 1332, the reception data is sent to the information processing terminal 50 (refer to FIG. 14) connected through the external I/F 136 or recorded in an external storage medium such as the portable storage medium 40 (refer to FIG. 14) attached to the external I/F 136, and the like. Further, when the reception data is image data, the image data can also be directly displayed on a display device such as a liquid crystal display and the like by providing a video output unit 137 as shown in FIG. 17.

The tilt angle detection circuit 134 is configured by including three Wheatstone bridge circuits for detecting resistance values as to, for example, an x-axis direction, a y-axis direction, and a z-axis direction, respectively and outputs a control signal for switching a connection destination of the antenna changeover switch 1311 to any of the dipole antennas 121a and 121b based on a ratio of the resistance values (that is, a direction of gravity or a tilt direction of the external antenna 120) obtained by the Wheatstone bridge circuits. At the time, the tilt angle detection circuit 134 outputs a control signal by which the dipole antenna 121a or 21b, which is in a state parallel with the ground surface or near to the parallel state, is selected. Note that the control signal can be, for example, a binary (for example, 1 bits) voltage signal. Further, detection of a tilt angle by the tilt angle detection circuit 134 is not limited to the configuration using the ratio of the resistance values described above and may be configured to previously determine relations between, for example, the resistances value of the respective x-axis, y-axis and z-axis and a tilt angle of the external antenna 120 by a measurement test and the like and to use the relations which are caused to correspond to each other in a table state.

As described above, the acceleration sensor 27 of the external antenna 120 and the tilt angle detection circuit 134 and the antenna changeover switch function as a selection means for selecting any of the plural polarized wave surfaces of the external antenna 120 in response to the tilt of the external antenna 120.

In addition to the above mentioned, when a control command and the like from the operation terminal 60 are input through, for example, a wired line, the input unit 135 can be composed of a USB interface and the like, and when the control command and the like from the operation terminal 60 are input through, for example, a wireless line of infrared rays, a short wave, a long wave, and the like, the input unit 135 can be composed of an infrared ray receiving device, a short/long wave receiving device, and the like. Further, when, for example, the portable storage medium 40 can be attached, the external I/F 136 can be composed of a USB interface and the like, and when the information processing terminal 50 can be connected through the communication cable 59, the external I/F 136 can be composed of a network interface and the like. However, the invention is not limited thereto and can be variously modified.

Positional Relation

Figure 18A:
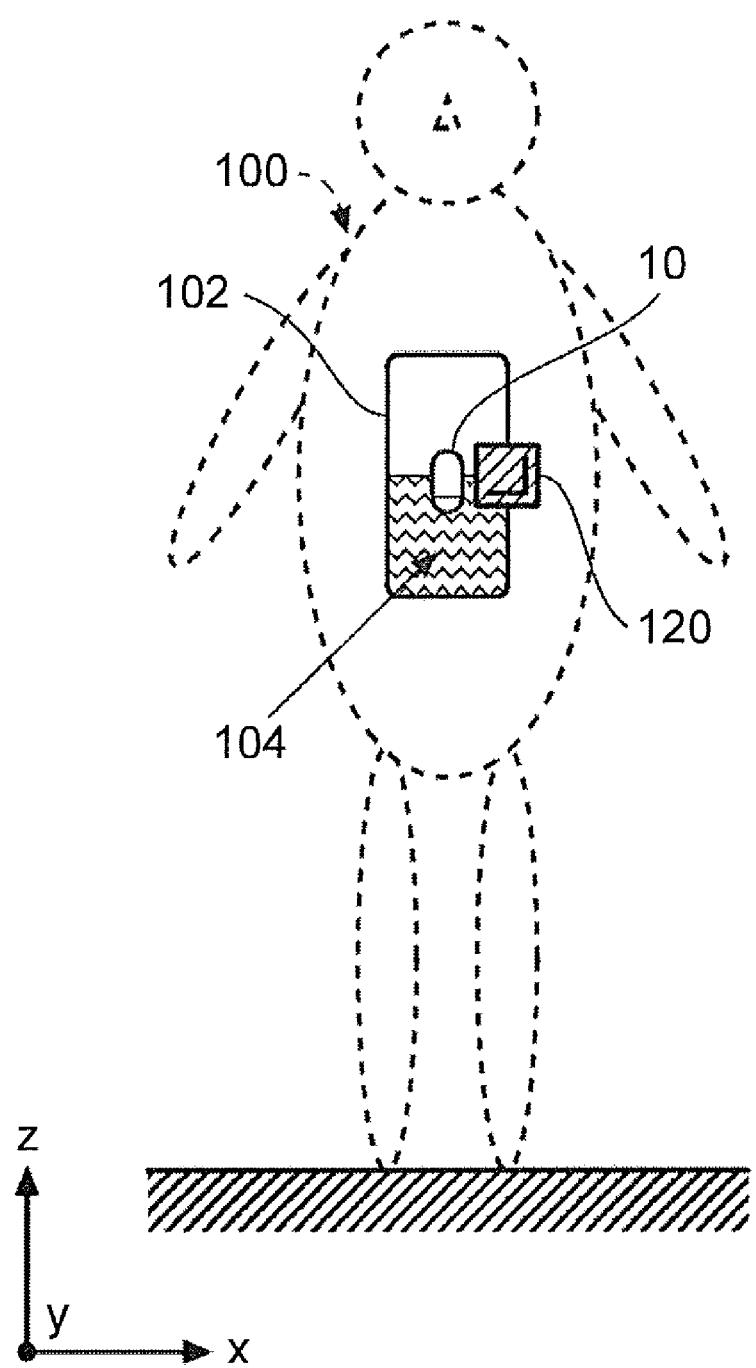
FIG. 18A is a schematic view explaining a positional relation between the capsule type medical apparatus introduced into the stomach of the subject and the external antenna attached to the outside surface of the subject in the first embodiment of the invention (standing position)
Figure 18B:
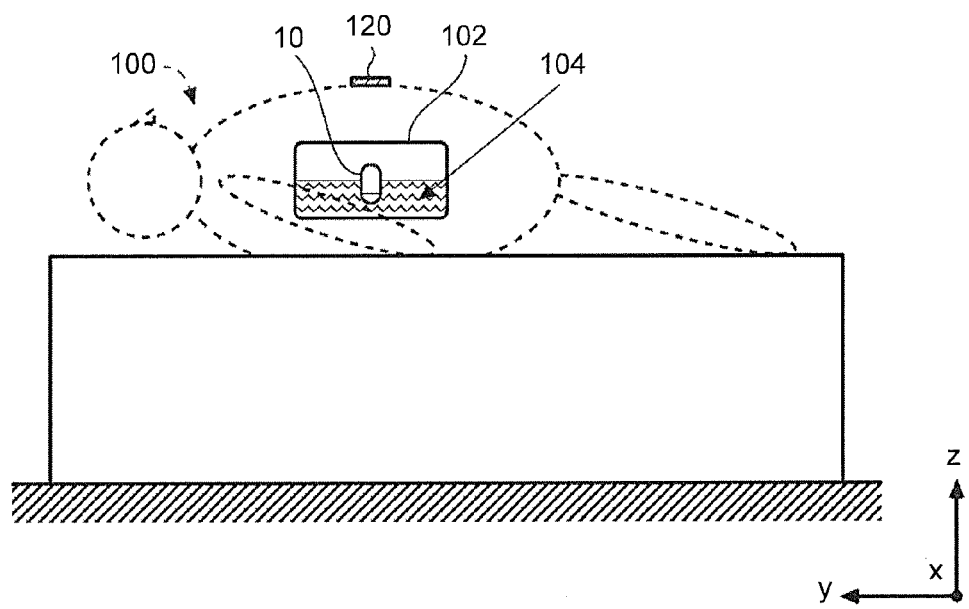
FIG. 18B is a schematic view explaining a positional relation between the capsule type medical apparatus introduced into the stomach of the subject and the external antenna attached to the outside surface of the subject in the first embodiment of the invention (back lying position)
Figure 18C:
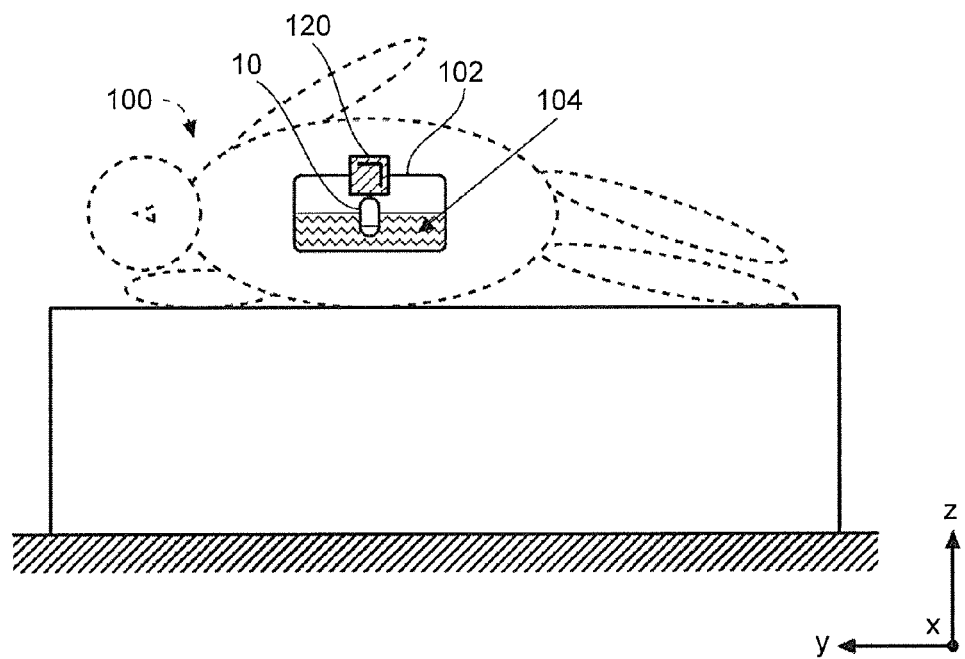
FIG. 18C is a schematic view explaining a positional relation between the capsule type medical apparatus introduced into the stomach of the subject and the external antenna attached to the outside surface of the subject in the first embodiment of the invention (right side lying position)

Next, a relation among a direction of the antenna 14a, a posture of the subject 100, and the external antenna 120 in the embodiment will be explained in detail with reference to the drawings. FIGS. 18A to 18C are schematic views explaining a positional relation between the capsule type medical apparatus 10 introduced into the stomach 102 of the subject 100 and the external antenna 120 attached to an outside surface of the subject 100. Note that, in the following explanation, the external antenna 120 is attached around a trunk of the subject 100. Further, in a state that the subject 100 takes a standing position, the dipole antenna 121a of the external antenna 120 extends in a horizontal direction (direction parallel to the ground surface), and the dipole antenna 121b extends in a vertical direction (direction vertical to the ground surface).

Further, the capsule type medical apparatus 10 in the subject 100 floats while keeping a posture on the liquid surface of the liquid 104 in the stomach 102 as described above. Accordingly, the winding axis of the antenna 14a disposed to the capsule type medical apparatus 10 keeps a predetermined direction at all times regardless of the posture of the subject 100 except an unstable state when the subject 100 changes a body position. In the embodiment, as shown in, for example, FIG. 15, the winding axis of the antenna 14a keeps a vertical direction (z-axis direction) to the ground surface. Accordingly, a vertical polarized wave of a radio wave output from the antenna 14a travels along a surface parallel with the z-axis, and a horizontal polarized wave travels along a surface parallel with the xy plane.

Standing Position (Sitting Position)

First, a case that the subject 100 takes a standing position will be explained. As shown in FIG. 18A, when the subject 100 takes the standing position, the dipole antenna 121a of the external antenna 120 extends in the horizontal direction (x-direction in FIG. 18A) parallel with the ground surface, and the dipole antenna 121b extends in the vertical direction (z-direction in FIG. 18A) to the ground surface. Accordingly, the dipole antenna 121a of the two dipole antennas 121a and 121b receives a horizontal polarized wave of a radio wave radiated from the antenna 14a, and the dipole antenna 121b receives a vertical polarized wave of the radio wave radiated from the antenna 14a. Thus, the tilt angle detection circuit 134 inputs a control signal by which the dipole antenna 121a is selected to the antenna changeover switch 1311. Note that the relation is also the same even when the subject 100 takes a sitting position posture.

Back Lying Position (Belly Lying Position)

Further, when the subject 100 takes a back lying position, as shown in FIG. 18B, the dipole antennas 121a and 121b of the external antenna 120 extend together in the horizontal direction (x-axis direction or y-axis direction in FIG. 18B) parallel with the ground surface. Accordingly, the two dipole antennas 121a and 121b can receive together the horizontal polarized wave of the radio wave radiated from the antenna 14a. Thus, in this case, a dipole antenna selected by the antenna changeover switch 1311 by the tilt angle detection circuit 134 may be any of the dipole antennas 121a and the dipole antenna 121b. Note that the relation is also the same even when the subject 100 takes a belly lying position (face down lying position).

Right Side Lying Position (Left Side Lying Position)

Further, when the subject 100 takes a right side lying position, as shown in FIG. 18C, the dipole antenna 121a of the external antenna 120 extends in the vertical direction (z-axis direction in FIG. 18C) to the ground surface, and the dipole antenna 121b extends in the horizontal direction (y-direction in FIG. 18C) parallel with the ground surface. Accordingly, the dipole antenna 121a of the two dipole antennas 121a and 121b receives the vertical polarized wave of the radio wave radiated from the antenna 14a, and the dipole antenna 121b receives the horizontal polarized wave of the radio wave radiated from the antenna 14a. Thus, the tilt angle detection circuit 134 inputs a control signal by which the dipole antenna 121b is selected to the antenna changeover switch 1311. Note that the relation is also the same even when the subject 100 takes a left side lying position.

As described above, according to the embodiment, since it is possible to configure the external antenna 120 so that the horizontal polarized wave is received using the external antenna 120 even when the subject 100 takes any posture, a reception efficiency can be prevented from being deteriorated by a body position of the subject 100. As a result, data can be accurately transmitted and received between the capsule type medical apparatus 10 and the external machine 130 without depending on a positional relation between the antenna 14*a* of the capsule type medical apparatus 10 and the external antenna 120 used by the external machine 130.

Modification 1

Figure 19A:
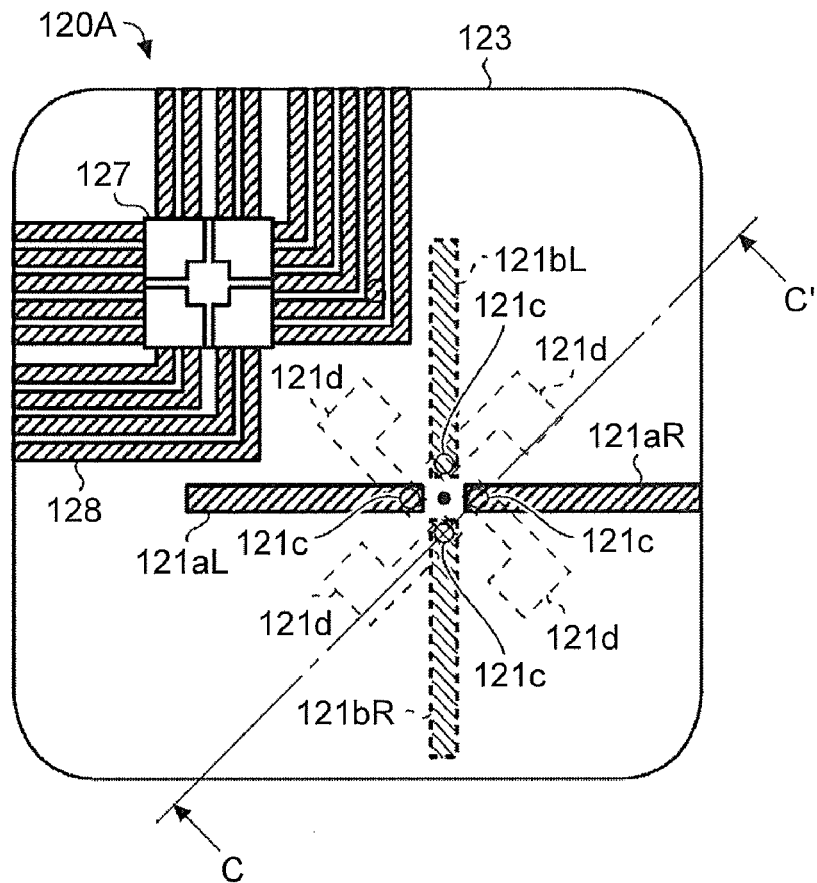
FIG. 19A is an upper view showing a schematic configuration of the external antenna according to the modification 1 of the first embodiment of the invention.
Figure 19B:
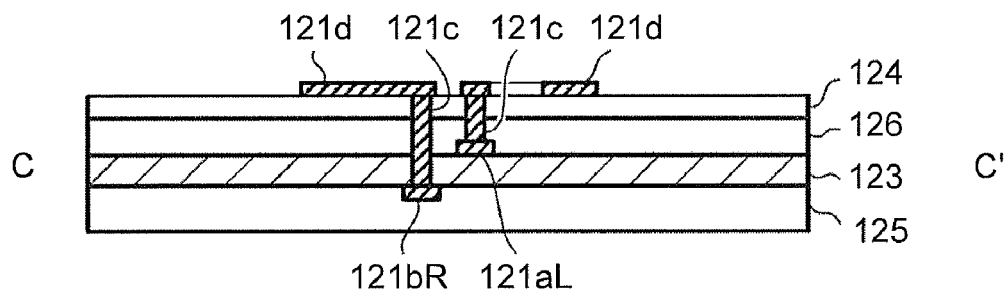
FIG. 19B is a C-C' sectional view of FIG. 19A.

Here, a modification 1 of the external antenna 120 according to the embodiment will be explained in detail with reference to the drawings. FIG. 19A is an upper view showing a schematic configuration of an external antenna 120A according to the modification. Further, FIG. 19B is a C-C' sectional view of FIG. 19A. Note that, in FIG. 21A, the cover film 124 for protecting an antenna portion and the spacer film 26 for securing a movable region of the spindle portion 27*c* of the acceleration sensor 27 are omitted to clarify explanation.

As shown in FIG. 19A, the external antenna 120A has such a configuration that elements 121*a*L and 121*a*R, which constitute a dipole antenna similar to the dipole antenna 121*a* of the external antenna 120 is formed on a diagonal line of a front surface of the flexible board 123 and the elements 121*b*L and 121*b*R, which constitute a dipole antenna 121*b* similar to the dipole antenna 121*b* of the external antenna 120 is formed on a diagonal line of a back surface of the flexible board 123. Note that an antenna composed of the elements 121*a*L and 121*a*R and an antenna composed of the elements 121*b*L and 121*b*R are disposed orthogonal to each other likewise the external antenna 120.

Further, as shown in FIGS. 19A and 19B, the respective elements 121*a*L, 121*a*R, 121*b*L, and 121*b*R are electrically connected to the electrode pads 121*d* on the cover film 124 through via contacts 121*c* passing through the cover film 124 on the front surface of the flexible board 123. In the modification, the connection cables 139 are bonded to the electrode pads 121*d* likewise the fifth embodiment of the invention.

With the configuration described above, the external antennas 20L and 20R can achieve the same effect as the external antenna 120. Note that since the other configurations are the same as the fifth embodiment of the invention described above, a detailed explanation is not repeated here.

Modification 2

Figure 20:
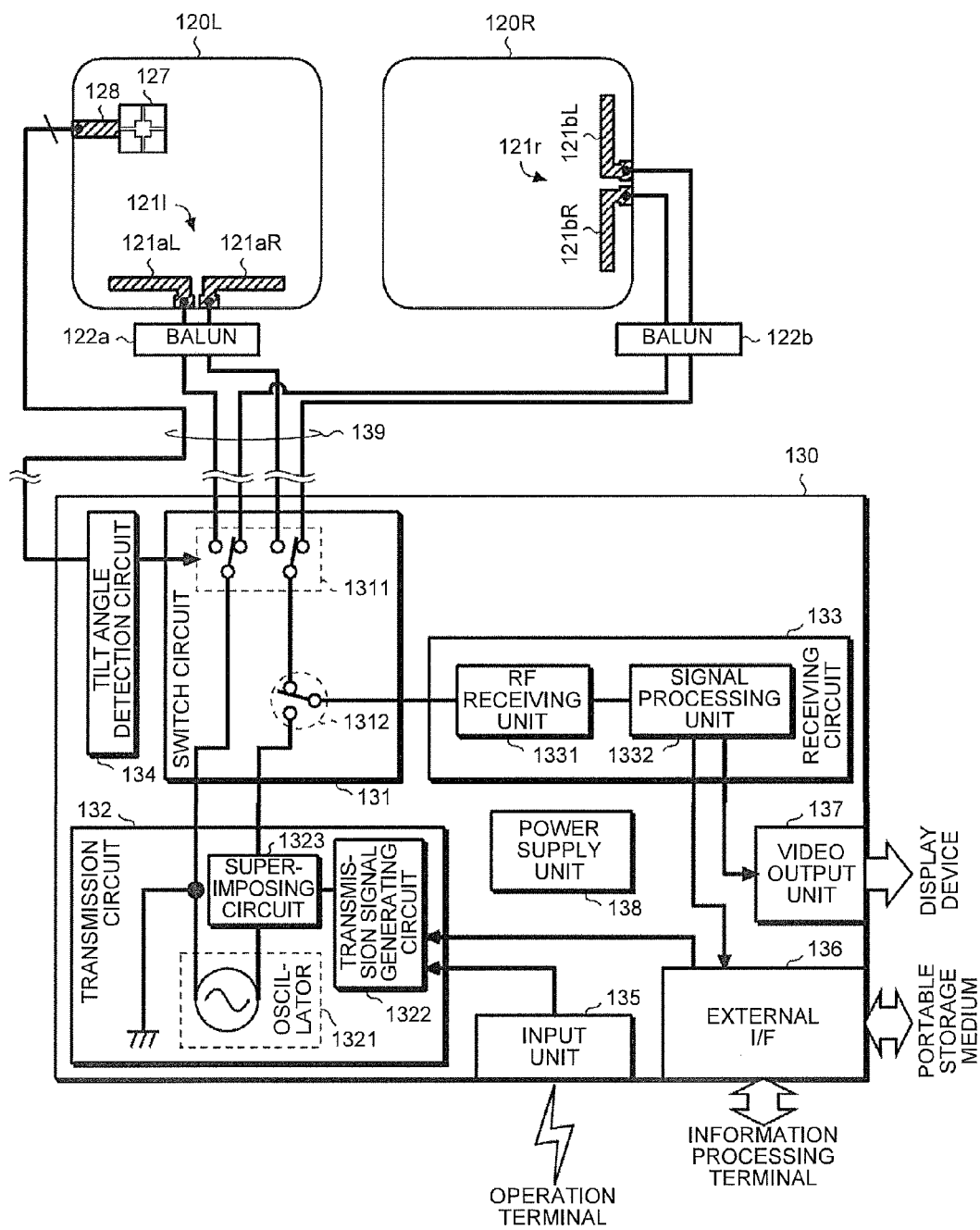
FIG. 20 is a schematic view showing a schematic configuration of the external antenna according to the modification 2 of the first embodiment of the invention.

Next, a modification 2 of the external antenna 120 according to the embodiment will be explained in detail with reference to the drawings. FIG. 20 is schematic view showing a schematic configuration of external antennas 120L and 120R according the modification. Note that, in FIG. 20, the external machine 130 connected to the external antennas 120L and 120R is also shown for the convenience of explanation.

As shown in FIG. 20, each of the external antennas 120L and 120R has one dipole antenna 121*l* or 21*r*. In the example, the external antenna 120L includes the dipole antenna 121*l* similar to the dipole antenna 121*a* of the external antenna 120, and the external antenna 120R includes the dipole antenna 121*r* similar to the dipole antenna 121*b* of the external antenna 120. Accordingly, a connection between the external antennas 120L and 120R and the external machine 130 is configured likewise the fifth embodiment of the invention.

Further, when the dipole antennas 121*a* and 121*b* are configured to different flexible boards 123 as described above, the acceleration sensor 27 may be formed on any of the flexible boards. In the modification, a case that the acceleration sensor 27 is formed on the external antenna 120L is exemplified as in FIG. 20.

With the configuration described above, the external antennas 120L and 120R can achieve the same effect as the external antenna 120. Further, since the two dipole antennas 121*a* and 121*b* can be greatly separated from each other as well as, when a radio wave is received, an influence, which is received by one dipole antenna from the other dipole antenna, can be reduced, a reception sensitivity (for example S/N ratio) can be prevented from being deteriorated by mutual interference. Note that since the other configurations are the same as the fifth embodiment of the invention described above, a detailed explanation is not repeated here.

Sixth Embodiment

Figure 21A:
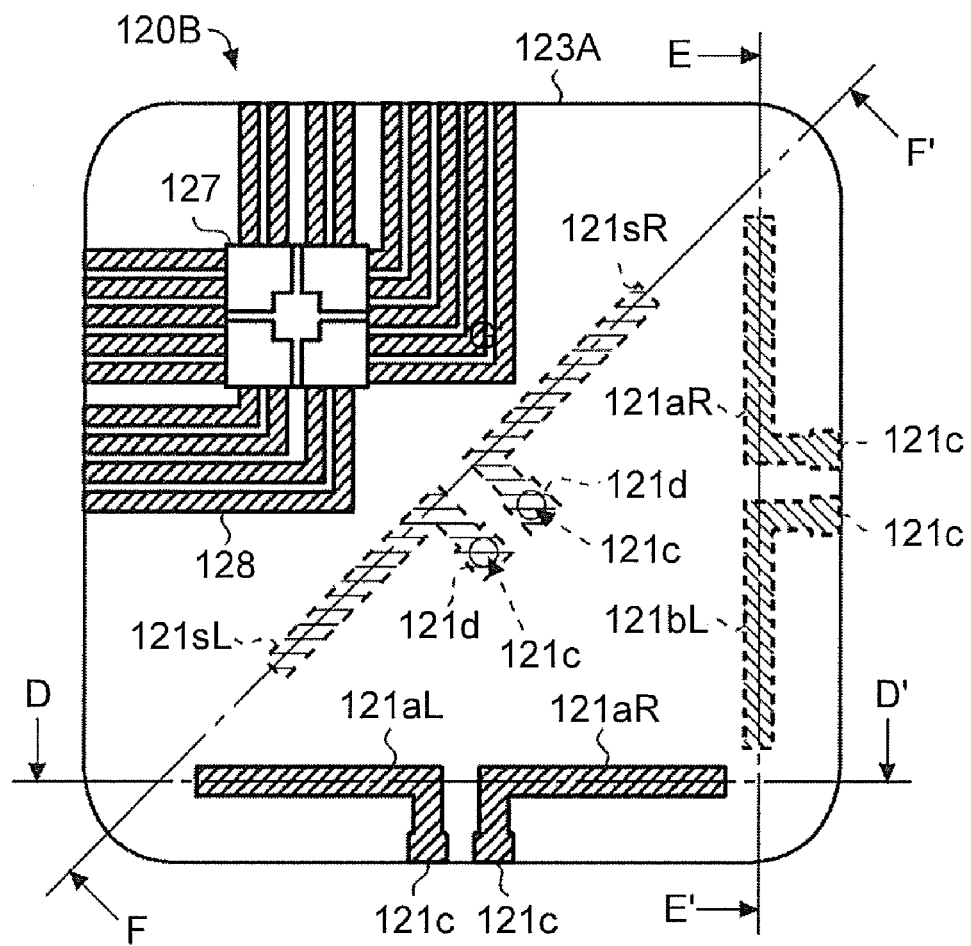
FIG. 21A is an upper view showing a schematic configuration of the external antenna according to the second embodiment of the invention.
Figure 21B:
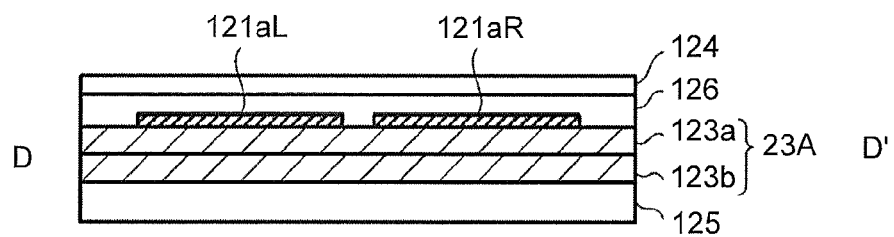
FIG. 21B is a D-D' sectional view of FIG. 21A.
Figure 21C:
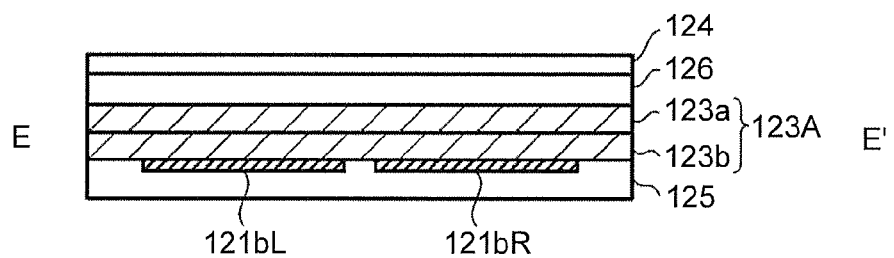
FIG. 21C is an E-E' sectional view of FIG. 21A.
Figure 21D:
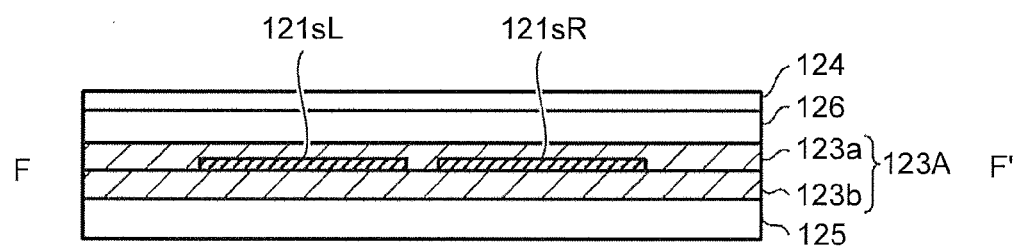
FIG. 21D is an F-F' sectional view of FIG. 21A.

Next, a medical system 6 according to a sixth embodiment of the invention will be explained in detail with reference to the drawings. FIG. 21A is an upper view showing a schematic configuration of an external antenna 120B according to the embodiment. Further, FIG. 21B is a D-D' sectional view of FIG. 21A, FIG. 21C is an E-E' sectional view of FIG. 21A, and FIG. 21D is an F-F' sectional view of FIG. 21A. Further, FIG. 22 is a schematic view showing a schematic configuration of the medical system 6 according to the embodiment. Note that, in FIG. 21A, the cover film 124 for protecting an antenna portion and a spacer film 126 for securing a movable region of a spindle portion 27*c* of the acceleration sensor 27 are omitted to clarify explanation.

As shown in FIG. 21A, the external antenna 120B includes dipole antennas 121*s* disposed on an extending surface of a flexible board 123A obliquely to the two dipole antennas 121*a* and 121*b* of the external antenna 120 in addition to the dipole antennas 121*a* and 121*b*. The dipole antennas 121*s* include two elements 121*s*L and 121*s*R disposed symmetrically likewise the other dipole antennas 121*a* and 121*b* and connected to an antenna changeover switch 1313 through a balun 122*s*.

Further, as shown in FIGS. 21B to 21D, the flexible board 123A according to the embodiment has a layered structure composed of two flexible boards 123*a* and 123*b*. As shown in FIG. 21B, the dipole antenna 121*a* is formed on, for example, a front surface of an uppermost layer of the flexible board 123A. Further, as shown in FIG. 21C, the dipole antenna 121*b* is formed on, for example, a back surface of a lowermost layer of the flexible board 123A. Further, as shown in, for example, FIG. 21D, the dipole antenna 121*s* is formed on a layer between, for example, the flexible boards 123*a* and 23*b*.

Further, the respective elements 121*s*L and 121*s*R of the dipole antenna 121*s* formed on an intermediate layer of the flexible board 123A are electrically connected to the electrode pads 121*d* on the cover film 124 through via contacts 121*c* passing through, for example, the flexible board 123*a* and through the cover film 124 on the flexible board 123A. In the embodiment, the connection cables 139 are bonded to the electrode pads 121*d* likewise the fifth embodiment of the invention.

In contrast, as shown in FIG. 22, in an external machine 130B according to the embodiment, the antenna changeover switch 1311 composed of the two 2-way switches in the external machine 130 is replaced with the antenna changeover switch 1313 composed of two 3-way switches. Further, a tilt angle detection circuit 134B for outputting a control signal for change-over controlling the antenna changeover switch 1313 is configured to output a control signal capable of controlling the two 3-way switches. Note that the control signal can be, for example, a 4-value (for example, 2 bits) voltage signal.

With the configuration described above, according to the embodiment, even when the subject 100 takes a tilt position, since a horizontal polarized wave can be received by the dipole antenna 121*s*, a reception strength, which is more securely stabilized, can be realized in addition to an effect similar to the fifth embodiment of the invention. Note that since the other configurations are the same as the fifth embodiment of the invention described above, a detailed explanation is not repeated here.

Seventh Embodiment

Figure 23:
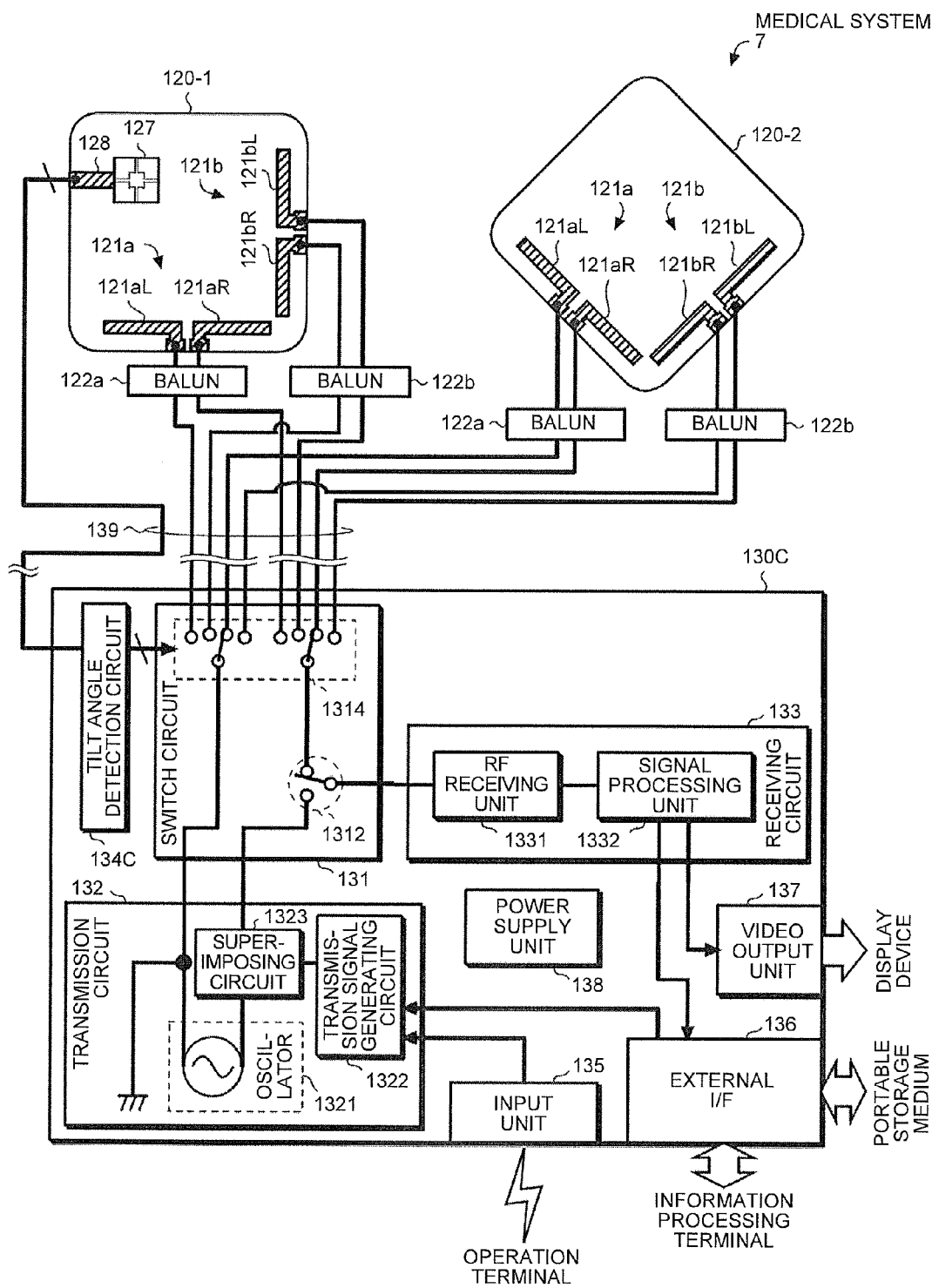
FIG. 23 is a schematic view showing a schematic configuration of the medical system according to the third embodiment of the invention.

Next, a medical system 7 according to a seventh embodiment of the invention will be explained in detail with reference to the drawings. FIG. 23 is a schematic view showing a schematic configuration of the medical system 7 according to the embodiment.

As shown in FIG. 23, the medical system 7 according to the embodiment uses two external antennas 120-1 and 120-2. Further, the external machine 130 of the medical system 5 is replaced with an external machine 130C in response to the configuration.

The respective external antennas 120-1 and 120-2 are the same as the external antenna 120 according to the fifth embodiment of the invention. However, in the embodiment, one external antenna 120-2 is bonded to the subject 100 so as to be oblique to the other the external antenna 120-1. That is, the dipole antenna 121*a* of the external antenna 120-1 tilts to dipole antennas 121*a* and 121*b* of the external antenna 120-2, and a dipole antenna 121*b* of the external antenna 120-1 tilts to the dipole antennas 121*a* and 121*b* of the external antenna 120-2 likewise. With this configuration, even when the subject 100 takes a tilt position, since a horizontal polarized wave can be received by any dipole antenna 121*a* or 21*b*, a reception strength, which is more securely stabilized, can be realized.

Further, the acceleration sensor 27 according to the embodiment may be disposed to any external antenna 120-1 or 20-2. In the embodiment, a case that the acceleration sensor 27 is disposed to the external antenna 120-1 is exemplified as shown in FIG. 23.

In contrast, as shown in FIG. 23, in the external machine 130C according to the embodiment, the antenna changeover switch 1311 composed of the two 2-way switches in the external machine 130 is replaced with an antenna changeover switch 1314 composed of two 4-way switches. Further, a tilt angle detection circuit 134C for outputting a control signal for changeover controlling the antenna changeover switch 1314 is configured to output a control signal capable of controlling the two 4-way switches. Note that the control signal can be, for example, a 4-value (for example, 2 bits) voltage signal.

With the configuration described above, according to the embodiment, even when the subject 100 takes the tilt position, since a horizontal polarized wave can be received by the dipole antenna 121*a* or 21*b* disposed to the external antenna 120-2, a reception strength, which is more securely stabilized, can be realized in addition to an effect similar to the fifth embodiment of the invention. Note that since the other configurations are the same as the fifth embodiment of the invention described above, a detailed explanation is not repeated here.

According to the embodiments described above, since an antenna polarized wave surface to be used for communication can be switched, even when the subject takes any posture, data can be transmitted and received using a polarized wave surface having an excellent reception sensitivity, in particular, using a horizontal polarized wave. With this operation, deterioration of the reception efficiency due to a body position of the subject can be prevented. As a result, a medical system, which can accurately transmit and receive data between a capsule type medical apparatus and an external machine without depending on a positional relation between a first antenna of the capsule type medical apparatus and an external antenna used by the external machine, an external device of the medical system and the capsule type medical apparatus of the medical system can be realized.

Further, according to the fifth and the sixth embodiments, that is, more specifically, since a polarized wave surface, which is used for communication, can be switched according to a tilt of the external antenna detected by the acceleration sensor, even when the subject takes any posture, data can be transmitted and received selecting a polarized wave surface having an excellent reception sensitivity, in particular a horizontal polarized wave. With this operation, deterioration of the reception efficiency due to a body position of the subject can be prevented. As a result, a medical system, which can accurately transmit and receive data between a capsule type medical apparatus and an external machine without depending on a positional relation between a first antenna of the capsule type medical apparatus and the external antenna used by the external machine, an external device of the medical system and the capsule type medical apparatus of the medical system can be realized.

For example, although the respective embodiments are configured to execute a communication selecting an antenna having a largest reception strength, the invention is not limited thereto, and, for example, the respective embodiments may be configured to select at least two antennas having a high reception strength and to combine signals received from the antennas. With this operation, an effect can be obtained in that, for example, directionality of an antenna used as the external antenna is suppressed by facing a direction in which directionality is maximized to a traveling direction of a desired wave as well as facing a direction in which directionality is deteriorated (null point) to a traveling direction of an interference wave and a position of the capsule type medical apparatus 10 in the subject 100 can be detected, and the like. Note that an ordinary adaptive array antenna technology, a phased array antenna technology, and the like can be used as a technology for combining the signals received by the at least two antennas.

Further, although the respective first to fourth embodiments described above exemplify a case that the plural antennas (dipole antennas 21*a*, 21*b*, and the like) have one polarized wave surface, respectively, the invention is not limited thereto and it is also possible to configure the respective embodiments so that the external antennas (20 and the like) are provided with plural polarized wave surfaces by switching, for example, polarized wave surfaces of one antenna by a switch. This can be realized by a configuration in which switches are disposed at, for example, two positions of a loop antenna and polarized wave surfaces are switched by switching connections of the switches, and the like.

Further, the respective fifth to seventh embodiments described above exemplify a case that the plural antennas (dipole antenna 121*a*, 121*b*, and the like) have one polarized wave surface, respectively. However, the invention is not limited thereto, and the respective fifth to seventh embodiments can also be configured so that external antennas (20 and the like) are provided with plural polarized wave surfaces by switching, for example, polarized wave surfaces of one antenna by a switch. This can be realized by a configuration in which switches are disposed at, for example, four positions of a loop antenna and polarized wave surfaces are switched by switching the connections of the switches, and the like.

As described above, according to the embodiment of the invention, since the polarized wave surfaces of the antenna to be used for communication can be switched, even when the subject takes any posture, data can be transmitted and received using a polarized wave surface having an excellent reception sensitivity, in particular, using the horizontal polarized wave. With this operation, deterioration of the reception efficiency due to a body position of the subject can be prevented. As a result, the medical system, which can accurately transmit and receive data between the capsule type medical apparatus and the external machine without depending on the positional relation between the first antenna of the capsule type medical apparatus and an external antenna used by the external machine, the external device of the medical system and the capsule type medical apparatus of the medical system can be realized.

The above and other features, advantages and technical and industrial significance of this invention will be better understood by reading the following detailed description of presently preferred embodiments of the invention, when considered in connection with the accompanying drawings.

What is claimed is:

1. A medical system comprising:
    a capsule type medical apparatus that is introduced into a subject and includes a first antenna which outputs a radio wave having directionality in a first polarized wave direction and a first communication unit which executes a communication through the first antenna;
    an external antenna that is disposed outside of the subject and includes a second antenna having directionality to a second polarized wave direction and a third antenna that is disposed together with the second antenna and has directionality to a third polarized wave direction different from the second polarized wave direction of the second antenna; and
    an external machine that includes a selection unit which selects any of the second and third antennas and a second communication unit which executes a communication with the first communication unit through the external antenna whose plane of polarization is selected by the selection unit, wherein
    the external antenna includes a board of a monolayer or multilayer structure on which the second and third antennas are formed, and
    the second antenna and the third antenna are formed on different planes or different layers in the board.

2. The medical system according to claim 1, wherein
    the external machine includes a reception strength detection unit that detects a reception strength on the plane of polarization selected by the selection unit, and
    the selection unit selects any of the second and third antennas based on the reception strength detected by the reception strength detection unit.

3. The medical system according to claim 1, wherein
    at least one of the second antenna and the third antenna is a dipole antenna, a loop antenna, or a micro strip antenna.

4. The medical system according to claim 1, wherein the board has a plastic property.

5. The medical system according to claim 1, comprising a plurality of external antennas,
    wherein the selection unit selects any of the second and third antennas as to each of the plurality of external antennas.

6. The medical system according to claim 1, wherein the external antenna is fixed to an outside surface of the subject.

7. The medical system according to claim 1, wherein a center of gravity of the capsule type medical apparatus is offset from a center.

8. The medical system according to claim 1, wherein the first antenna is a coil antenna.

9. The medical system according to claim 1, further comprising:
    a sensor that detects a tilt angle of the external antenna to the ground surface;
    wherein the selection unit selects any of the second and third antennas in response to the tilt angle detected by the sensor, and the second communication unit executes a communication with the first communication unit through the external antenna whose plane of polarization is selected by the selection unit.

10. The medical system according to claim 9, wherein the external antenna and the sensor are formed on the same board.

11. The medical system according to claim 9, wherein
    at least one of the second antenna and the third antenna is a dipole antenna, a loop antenna, or a micro strip antenna.

12. The medical system according to claim 9 wherein:
    the second antenna and the third antenna are formed on different boards, respectively; and
    the sensor is formed on a board on which the second antenna is formed or on a board on which the third antenna is formed.

13. The medical system according to claim 9, wherein the board has a plastic property.

14. The medical system according to claim 9 comprising a plurality of external antennas, wherein
    the selection unit selects any of the second and third antennas as to each of the plurality of external antennas; and
    the sensor is formed on the same board as a board of any of the plurality of external antennas.

15. The medical system according to claim 9, wherein the external antenna is fixed to an outside surface of the subject.

16. The medical system according to claim 9, wherein a center of gravity of the capsule type medical apparatus is offset from a center.

17. The medical system according to claim 9, wherein the first antenna is a coil antenna.

* * * * *